US012767634B2

(12) United States Patent
Jung et al.

(10) Patent No.: US 12,767,634 B2
(45) Date of Patent: Oct. 20, 2026

(54) OPTICAL ABSORBENT COMPOSITION

(71) Applicant: LMS CO., LTD., Pyeongtaek-si (KR)

(72) Inventors: Joon Ho Jung, Pyeongtaek-si (KR); Hee Kyeong Kim, Pyeongtaek-si (KR)

(73) Assignee: LMS CO., LTD., Pyeongtaek-si (KR)

( * ) Notice: Subject to any disclaimer, the term of this patent is extended or adjusted under 35 U.S.C. 154(b) by 519 days.

(21) Appl. No.: 18/519,160

(22) Filed: Nov. 27, 2023

(65) Prior Publication Data

US 2024/0199547 A1 Jun. 20, 2024

(30) Foreign Application Priority Data

Dec. 7, 2022 (KR) ........................ 10-2022-0169674

(51) Int. Cl.

| | |
|---|---|
| ***C07D 209/40*** | (2006.01) |
| ***C07D 209/60*** | (2006.01) |
| ***C09D 5/32*** | (2006.01) |
| ***C09D 7/41*** | (2018.01) |
| ***C09D 7/63*** | (2018.01) |
| ***C09D 133/12*** | (2006.01) |

(Continued)

(52) U.S. Cl.

CPC ......... *C07D 209/40* (2013.01); *C07D 209/60* (2013.01); *C09D 5/32* (2013.01); *C09D 7/41* (2018.01); *C09D 7/63* (2018.01); *C09D 133/12* (2013.01); *C09D 145/00* (2013.01); *C09D 183/04* (2013.01); *C09D 201/00* (2013.01); *G02B 5/003* (2013.01); *G02B 5/208* (2013.01); *G02B 5/22* (2013.01); *G02B 5/223* (2013.01); *H04N 25/10* (2023.01); *C09B 57/007* (2013.01); *G02B 1/04* (2013.01)

(58) Field of Classification Search

CPC .. C09D 145/00; C09D 183/04; C09D 133/12; C08K 5/3417

See application file for complete search history.

(56) References Cited

U.S. PATENT DOCUMENTS

| | | | | |
|---|---|---|---|---|
| 2014/0061505 A1* | 3/2014 | Steppel | .................... | G02B 5/00 250/200 |
| 2017/0115561 A1 | 4/2017 | Yang et al. | | |

(Continued)

FOREIGN PATENT DOCUMENTS

| | | |
|---|---|---|
| CN | 101836275 A | 9/2010 |
| CN | 103053223 A | 4/2013 |

(Continued)

*Primary Examiner* — Eli D. Strah

(74) *Attorney, Agent, or Firm* — NKL LAW; Jae Youn Kim

(57) ABSTRACT

The present invention provides an optical absorbent composition and its use. In the present invention, it is possible to provide the optical absorbent composition, as an optical absorbent composition containing two or more kinds of absorbents, exhibiting excellent compatibility or solubility with respect to various solvents and resin components. In the present invention, it is possible to obtain desired optical properties by applying the optical absorbent composition. The purpose of the present invention is also to provide applications for the optical absorbent composition. For example, an optical absorption film, an optical filter, a solid-state image capturing device, and/or an infrared sensor may be provided by using the optical absorbent composition.

20 Claims, 4 Drawing Sheets

(51) Int. Cl.

| | |
|---|---|
| ***C09D 145/00*** | (2006.01) |
| ***C09D 183/04*** | (2006.01) |
| ***C09D 201/00*** | (2006.01) |
| ***G02B 5/00*** | (2006.01) |
| ***G02B 5/20*** | (2006.01) |
| ***G02B 5/22*** | (2006.01) |
| ***H04N 25/10*** | (2023.01) |
| *C09B 57/00* | (2006.01) |
| *G02B 1/04* | (2006.01) |

(56) References Cited

U.S. PATENT DOCUMENTS

| | | | | |
|---|---|---|---|---|
| 2020/0200956 | A1* | 6/2020 | Shiono | G02B 5/282 |
| 2021/0191013 | A1* | 6/2021 | Moon | C08K 5/29 |

FOREIGN PATENT DOCUMENTS

| | | | |
|---|---|---|---|
| CN | 108474884 | A | 8/2018 |
| CN | 111095045 | A | 5/2020 |
| CN | 111770968 | A | 10/2020 |
| CN | 113721316 | A | 11/2021 |
| JP | 2016045372 | A | 4/2016 |
| JP | 2021047325 | A | 3/2021 |
| JP | 2022067588 | A | 5/2022 |
| KR | 10-2022-0073996 | A | 6/2022 |
| TW | 201213894 | A | 4/2012 |
| WO | 2018100834 | A1 | 6/2018 |
| WO | 2019039159 | A1 | 2/2019 |
| WO | 2019054135 | A1 | 3/2019 |
| WO | 2021049441 | A1 | 3/2021 |
| WO | 2022085636 | A1 | 4/2022 |

* cited by examiner

OPTICAL ABSORBENT COMPOSITION

CROSS-REFERENCE TO RELATED APPLICATION(S)

The present application is based on and claims priority under 35 U.S.C. 119 to Korean Patent Application No. 10-2022-0169674, filed on Dec. 7, 2022, in the Korean Intellectual Property Office, the disclosure of which is herein incorporated by reference in its entirety.

TECHNICAL FIELD

The present invention relates to an optical absorbent composition and its use.

BACKGROUND

An optical absorbent, for example, an absorbent capable of absorbing light in the infrared region can be applied to various applications. For example, because an image capturing device or an infrared sensor using a CCD (Charge-Coupled Device) or a CMOS (Complementary Metal-Oxide-Semiconductor) image sensor include a silicon photodiode having sensitivity to the near-infrared region, the optical absorbent may be used for them.

Although there are various methods of applying such an optical absorbent, a method of using coating solution where an optical absorbent dissolved in a solvent and a resin component are mixed is generally applied. Therefore, the optical absorbent needs to exhibit excellent solubility or compatibility with both the solvent and the resin component.

If the solubility or compatibility of the optical absorbent with respect to the solvent or resin component is poor, desired spectral characteristics cannot be obtained for an optical absorption film where the optical absorbent is applied, or its optical properties are deteriorated due to precipitation of the optical absorbent in the optical absorption film. However, it is a difficult task to obtain an optical absorbent that exhibits excellent solubility or compatibility with various types of solvents and resin components at the same time.

In addition, for example, when an wide absorption band width is wide or other optical properties which are difficult to obtain with a single optical absorbent are required, two or more kinds of optical absorbents must be applied. It is a difficult task for two or more kinds of absorbents to exhibit excellent solubility or compatibility with respect to various types of solvents and resin components at the same time.

SUMMARY

An object of the present invention provides an optical absorbent composition and its use. Furthermore, the object of the present invention provides the optical absorbent composition containing two or more kinds of optical absorbents and exhibiting excellent compatibility or solubility with respect to various solvents and resin components.

Another object of the present invention is to obtain desired optical characteristics by applying the optical absorbent composition.

Another object of the present invention is to provide an application for the optical absorbent composition. For example, the object of the present invention is to provide applications such as an optical absorption film formed by using the optical absorbent composition, an optical filter, a solid-state image capturing device, and/or an infrared sensor.

According to an embodiment of the invention, there is provided that an optical absorbent composition comprises a first chemical compound represented by Chemical Formula 1

[Chemical Formula 1]

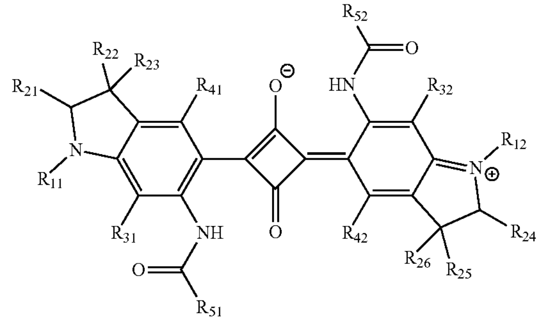

wherein $R_{11}$, $R_{12}$, $R_{51}$ and $R_{52}$ are each independently an alkyl group, a haloalkyl group, an alkoxy group, or an alkoxyalkyl group and $R_{21}$, $R_{22}$, $R_{23}$, $R_{24}$, $R_{25}$, $R_{26}$, $R_{31}$, $R_{32}$, $R_{41}$ and $R_{42}$ are each independently hydrogen, an alkyl group, an alkoxy group, or an alkoxyalkyl group in Chemical Formula 1, wherein the first chemical compound satisfies any one of Condition 1 and Condition 2:

Condition 1: a sum of carbon numbers of $R_{11}$, $R_{12}$, $R_{51}$, $R_{52}$, $R_{21}$, $R_{22}$, $R_{23}$, $R_{24}$, $R_{25}$, $R_{26}$, $R_{31}$, $R_{32}$, $R_{41}$ and $R_{42}$ in Chemical Formula 1 is 16 or more; and Condition 2: a sum of carbon numbers of $R_{11}$, $R_{12}$, $R_{51}$, $R_{52}$, $R_{21}$, $R_{22}$, $R_{23}$, $R_{24}$, $R_{25}$, $R_{26}$, $R_{31}$, $R_{32}$, $R_{41}$ and $R_{42}$ in Chemical Formula 1 is 14 or more, and at least one of $R_{11}$, $R_{12}$, $R_{51}$, $R_{52}$, $R_{21}$, $R_{22}$, $R_{23}$, $R_{24}$, $R_{25}$, $R_{26}$, $R_{31}$, $R_{32}$, $R_{41}$ and $R_{42}$ is an alkoxy group or an alkoxyalkyl group; and a second chemical compound represented by Chemical Formula 2:

[Chemical Formula 2]

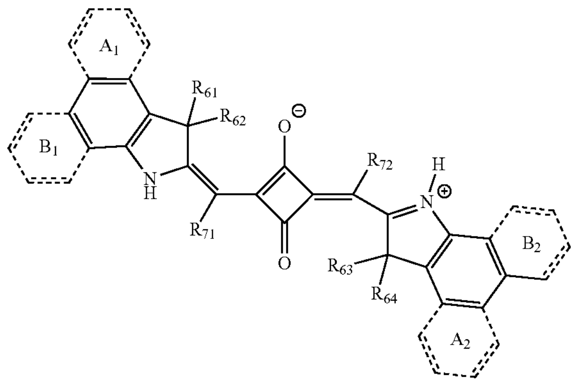

wherein $R_{71}$ and $R_{72}$ are each independently an alkyl group, an alkoxy group, or an alkoxyalkyl group, $R_{61}$ to $R_{64}$ are each independently hydrogen, an alkyl group, an alkoxy group, or an alkoxyalkyl group, and $A_1$, $B_1$, $A_2$ and $B_2$ are each independently a benzene structure or absent in Chemical Formula 2, wherein the second chemical compound satisfies any one of Condition 3 and Condition 4:

Condition 3: a sum of carbon numbers of $R_{61}$, $R_{62}$, $R_{63}$, $R_{64}$, $R_{71}$ and $R_{72}$ in Chemical Formula 2 is 10 or more; and Condition 4: a sum of carbon numbers of $R_{61}$, $R_{62}$, $R_{63}$, $R_{64}$, $R_{71}$ and $R_{72}$ is 4 or more, and at least one of $R_{61}$, $R_{62}$, $R_{63}$, $R_{64}$, $R_{71}$, and $R_{72}$ is an alkoxy group or an alkoxyalkyl group in Chemical Formula 2.

In an embodiment, $R_{21}$, $R_{22}$, $R_{23}$, $R_{24}$, $R_{25}$ and $R_{26}$ in Chemical Formula 1 are each independently an alkyl group, an alkoxy group, or an alkoxyalkyl group and $R_{31}$, $R_{32}$, $R_{41}$ and $R_{42}$ is hydrogen for the optical absorbent composition in the present invention.

In an embodiment, a ratio (C1/C5) of a sum of carbon numbers of $R_{11}$ and $R_{12}$ (C1) to a sum of carbon numbers of $R_{51}$ and $R_{52}$ (C5) in Chemical Formula 1 is in a range of 0.1 to 10 for the optical absorbent composition in the present invention.

In an embodiment, a ratio (C1/C2) of a sum of carbon numbers of Ru and $R_{12}$ (C1) to a sum of carbon numbers of $R_{21}$ to $R_{26}$, $R_{31}$, $R_{32}$, $R_{41}$ and $R_{42}$ (C2) in Chemical Formula 1 is in a range of 1 to 10 for the optical absorbent composition in the present invention.

In an embodiment, a ratio (C11/C12) of a carbon number of $R_{11}$ (C11) to a carbon number of $R_{12}$ (C12) in Chemical Formula 1 is in a range of 0.1 to 2 for the optical absorbent composition in the present invention.

In an embodiment, a ratio (C51/C52) of a carbon number of $R_{51}$ (C51) to a carbon number of $R_{52}$ (C52) in Chemical Formula 1 is in a range of 0.1 to 2 for the optical absorbent composition in the present invention.

In an embodiment, a ratio (C7/C6) of a sum of carbon numbers of $R_{71}$ and $R_{72}$ (C7) to a sum of carbon numbers of $R_{61}$ to $R_{64}$ (C6) in Chemical Formula 2 is in a range of 0.1 to 10 for the optical absorbent composition in the present invention.

In an embodiment, a ratio (C71/C72) of a carbon number of $R_{71}$ (C71) to a carbon number of $R_{72}$ (C72) in Chemical Formula 2 is in a range of 0.1 to 2 for the optical absorbent composition in the present invention.

In an embodiment, one of $A_1$ and $B_1$ is a benzene structure and the other is absent, and one of $A_2$ and $B_2$ is a benzene structure and the other is absent in Chemical Formula 2 for the optical absorbent composition in the present invention.

In an embodiment, a ratio (C1/C7) of a sum of carbon numbers of Ruu and $R_{12}$ (C1) in Chemical Formula 1 to a sum of carbon numbers of $R_{71}$ and $R_{72}$ (C7) in Chemical Formula 2 is in a range of 0.1 to 10 for the optical absorbent composition in the present invention.

In an embodiment, a sum of carbon numbers of $R_{11}$, $R_{12}$, $R_{51}$, $R_{52}$, $R_{21}$, $R_{22}$, $R_{23}$, $R_{24}$, $R_{25}$, $R_{26}$, $R_{31}$, $R_{32}$, $R_{41}$, $R_{42}$, $R_{61}$, $R_{62}$, $R_{63}$, $R_{64}$, $R_{71}$ and $R_{72}$ is 30 or more for the optical absorbent composition in the present invention.

In an embodiment, a ratio (CA/CB) of a sum of carbon numbers of $R_{11}$, $R_{12}$, $R_{51}$, $R_{52}$, $R_{21}$, $R_{22}$, $R_{23}$, $R_{24}$, $R_{25}$, $R_{26}$, $R_{31}$, $R_{32}$, $R_{41}$ and $R_{42}$ (CA) to a sum of carbon numbers of $R_{61}$, $R_{62}$, $R_{63}$, $R_{64}$, $R_{71}$ and $R_{72}$ (CB) is in a range of 0.5 to 5 for the optical absorbent composition in the present invention.

In an embodiment, the optical absorbent composition comprises 1 to 500 parts by weight of the second chemical compound with respect to 100 parts by weight of the first chemical compound in the present invention.

In an embodiment, the optical absorbent composition further comprises a resin component in the present invention.

In an embodiment, the optical absorbent composition further comprises a solvent in the present invention.

According to another embodiment of the invention, there is provided that an optical absorption film comprises a resin, a third chemical compound represented by Chemical Formula 1:

[Chemical Formula 1]

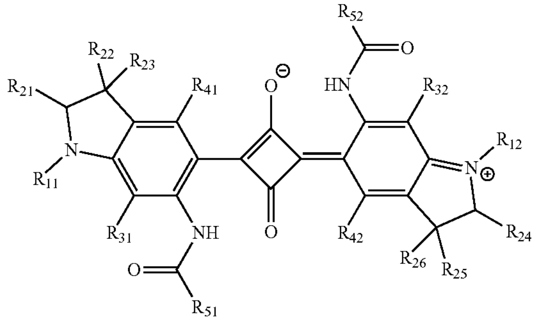

wherein $R_{11}$, $R_{12}$, $R_{51}$ and $R_{52}$ are each independently an alkyl group, haloalkyl group, alkoxy group or alkoxyalkyl group, and $R_{21}$, $R_{22}$, $R_{23}$, $R_{24}$, $R_{25}$, $R_{26}$, $R_{31}$, $R_{32}$, $R_{41}$ and $R_{42}$ are each independently hydrogen, an alkyl group, an alkoxy group, or an alkoxyalkyl group in Chemical Formula 1; and a fourth chemical compound represented by Chemical Formula 2:

[Chemical Formula 2]

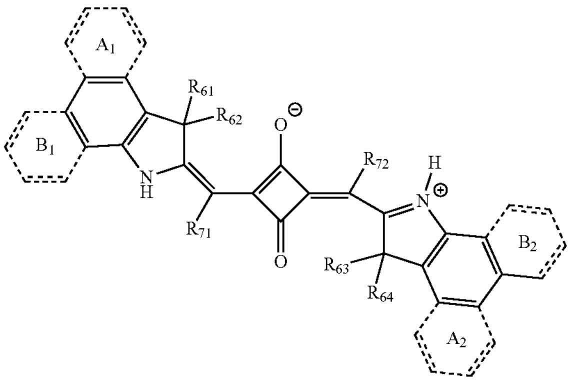

wherein $R_{71}$ and $R_{72}$ are each independently an alkyl group, an alkoxy group, or an alkoxyalkyl group, $R_{61}$ to $R_{64}$ are each independently hydrogen, an alkyl group, an alkoxy group, or an alkoxyalkyl group, and $A_1$, $B_1$, $A_2$ and $B_2$ are each independently a benzene structure or absent in Chemical Formula 2.

In another embodiment, an absorption band exhibits a bandwidth of 60 nm or more in a wavelength range of 600 nm to 900 nm for the optical absorption film in the present invention.

In another embodiment, the resin component comprises one or more selected from a group consisted of a cyclo olefin polymer (COP)-based resin, polyarylate resin, polysulfone resin, polyether sulfone resin, polyparaphenylene resin, polyarylene ether phosphine oxide resin, polyimide resin, polyetherimide resin, polyamideimide resin, acrylic resin, polycarbonate resin, polyethylene naphthalate resin, and silicone resin for the optical absorption film in the present invention.

In another embodiment, T50% cut-on wavelength is in a wavelength range of 600 nm to 800 nm for the optical absorption film in the present invention.

In another embodiment, T50% cut-off wavelength is in a wavelength range of 700 nm to 900 nm for the optical absorption film in the present invention.

In another embodiment, the optical absorption film comprises 0.5 to 50 parts by weight of the third chemical compound with respect to 100 parts by weight of the resin component in the present invention.

In another embodiment, the optical absorption film comprises 0.5 to 50 parts by weight of the fourth chemical compound with respect to 100 parts by weight of the resin component in the present invention.

According to another embodiment of the invention, there is provided that an optical filter comprises a substrate and an optical absorption film formed on one or both surfaces of the substrate wherein the optical absorption film further comprises a resin, a fifth chemical compound represented by Chemical Formula 1:

[Chemical Formula 1]

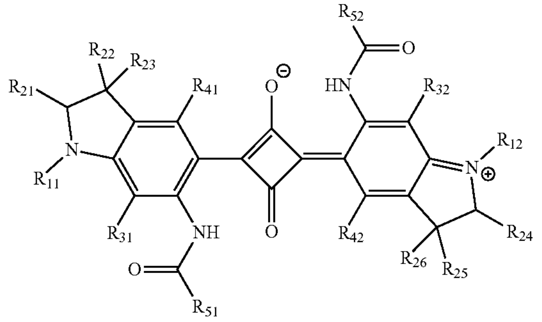

wherein $R_{11}$, $R_{12}$, $R_{51}$ and $R_{52}$ are each independently an alkyl group, a haloalkyl group, an alkoxy group, or an alkoxyalkyl group and $R_{21}$, $R_{22}$, $R_{23}$, $R_{24}$, $R_{25}$, $R_{26}$, $R_{31}$, $R_{32}$, $R_{41}$ and $R_{42}$ are each independently hydrogen, an alkyl group, an alkoxy group, or an alkoxyalkyl group in Chemical Formula 1, and a sixth chemical compound represented by Chemical Formula 2:

[Chemical Formula 2]

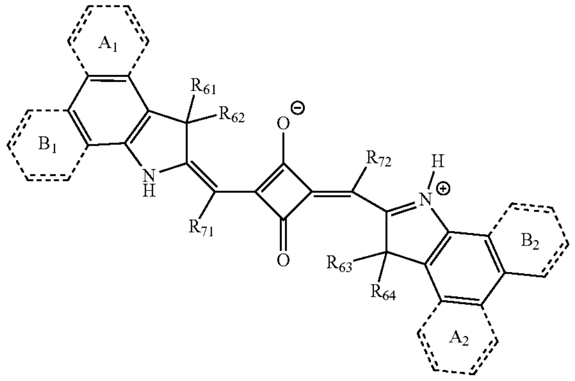

wherein $R_{71}$ and $R_{72}$ are each independently an alkyl group, an alkoxy group, or an alkoxyalkyl group, $R_{61}$ to $R_{64}$ are each independently hydrogen, an alkyl group, an alkoxy group, or an alkoxyalkyl group, and $A_1$, $B_1$, $A_2$ and $B_2$ are each independently a benzene structure or absent in Chemical Formula 2.

In another embodiment, the optical filter further comprises a dielectric film wherein a shortest wavelength exhibiting a reflectance of 50% in a wavelength range of 600 nm to 900 nm in the dielectric film is 710 nm or more or absent.

According to another embodiment of the invention, there is provided that an image capturing device comprises the optical filter.

According to another embodiment of the invention, there is provided that an infrared sensor comprises the optical absorption film.

DETAILED DESCRIPTION

Figure 1:
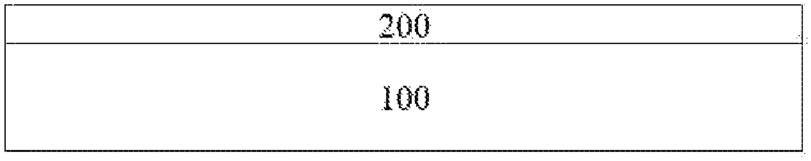
FIGS. 1 to 3 are schematics showing an exemplary structure of an optical filter of the present invention.

Various embodiments and terms used in the specification are not intended to limit the technical features described in the specification to specific embodiments, but it should be understood to include various modifications, equivalents, or substitutions of the embodiments. In connection with the description of the drawings, similar reference numerals may be used for similar or related components. The singular form of the noun corresponding to the item may include one or more of the elements unless the relevant context clearly dictates otherwise.

Embodiments will be described with reference to the associating drawings. In describing the present embodiment, the same names and the same reference numerals are used for the same components, and an additional description thereof will be omitted. In addition, in describing the embodiment of the present invention, the same names and reference numerals are used for components having the same functions, and it is substantially not completely the same as in the prior art.

According to various embodiments, terms such as "comprise" or "have" are intended to designate the presence of a feature, number, step, operation, component, part, or combination described in the specification. It should be understood, however, that the above does not preclude the possibility of addition or existence of one or more of other features, or numbers, steps, operations, components, parts, or combinations.

For those physical properties mentioned in the specification where the result of measuring temperature may affect, it is measured at room temperature unless otherwise specified. The term "room temperature" used in the specification refers to a natural temperature that is not heated or not reduced, for example, it means any temperature within the range of 10° C. to 30° C., a temperature of about 23° C. or about 25° C. In addition, in the specification, the unit of temperature is Celsius (° C.) unless otherwise specified.

For those physical properties mentioned in the specification where the result of measuring pressure may affect, it is measured at atmospheric pressure unless otherwise specified. The term "atmospheric pressure" is a natural pressure that is not pressurized or depressurized. It usually means about 1 atmosphere of atmospheric pressure having the value of about 740 mmHg to 780 mmHg.

In the specification, in case of a physical property in which the measured humidity affects the result, the physical property is a physical property measured at natural humidity that is not specifically controlled at the room temperature and/or atmosphere pressure.

In the case where an optical characteristic (e.g., refractive index) referred to in the present invention is a characteristic that varies depending on the wavelength, the optical characteristic is a result obtained for light having a wavelength of 520 nm unless otherwise specified.

The term "transmittance," "reflectance," or "absorbance" used in the present invention means an actual transmittance (measured transmittance), an actual reflectance (measured reflectance), or an actual absorbance (measured absorbance) confirmed at a specific wavelength unless otherwise specified.

The term "transmittance," "reflectance," or "absorbance" used in the present invention is a value measured using an ultraviolet and visible spectrophotometer and means the transmittance, the reflectance, or the absorbance for light at an incident angle of 0° based on the normal of the measurement target surface unless the incident angle is specifically specified.

In the present invention, the term "average transmittance" is a result of obtaining an arithmetic average of the measured transmittances after measuring transmittance of each wavelength while increasing the wavelength by 1 nm from the shortest wavelength within a predetermined wavelength region unless otherwise specified. For example, the average transmittance within the wavelength range of 350 nm to 360 nm is an arithmetic average of transmittance measured at the wavelength of 350 nm, 351 nm, 352 nm, 353 nm, 354 nm, 355 nm, 356 nm, 357 nm, 358 nm, 359 nm and 360 nm.

In the specification, the term "maximum transmittance" refers to the maximum transmittance when the transmittance of each wavelength is measured while increasing the wavelength by 1 nm from the shortest wavelength within a predetermined wavelength region. For example, the maximum transmittance within the wavelength range of 350 nm to 360 nm is the highest transmittance among transmittances measured at the wavelength of 350 nm, 351 nm, 352 nm, 353 nm, 354 nm, 355 nm, 356 nm, 357 nm, 358 nm, 359 nm and 360 nm.

In the present invention, the term "average reflectance" is a result of obtaining an arithmetic average of the measured reflectances after measuring reflectance of each wavelength while increasing the wavelength by 1 nm from the shortest wavelength within a predetermined wavelength region unless otherwise specified. For example, the average reflectance within the wavelength range of 350 nm to 360 nm is an arithmetic average of reflectance measured at the wavelength of 350 nm, 351 nm, 352 nm, 353 nm, 354 nm, 355 nm, 356 nm, 357 nm, 358 nm, 359 nm and 360 nm.

In the specification, the term "maximum reflectance" refers to the maximum reflectance when the reflectance of each wavelength is measured while increasing the wavelength by 1 nm from the shortest wavelength within a predetermined wavelength region. For example, the maximum reflectance within the wavelength range of 350 nm to 360 nm is the highest reflectance among reflectances measured at the wavelength of 350 nm, 351 nm, 352 nm, 353 nm, 354 nm, 355 nm, 356 nm, 357 nm, 358 nm, 359 nm and 360 nm.

In the present invention, the term "average absorbance" is a result of obtaining an arithmetic average of the measured average absorbances after measuring absorbance of each wavelength while increasing the wavelength by 1 nm from the shortest wavelength within a predetermined wavelength region unless otherwise specified. For example, the average absorbance within the wavelength range of 350 nm to 360 nm is an arithmetic average of absorbance measured at the wavelength of 350 nm, 351 nm, 352 nm, 353 nm, 354 nm, 355 nm, 356 nm, 357 nm, 358 nm, 359 nm and 360 nm.

In the present specification, the term "maximum absorbance" refers to the maximum absorbancewhen the absorbanceof each wavelength is measured while increasing the wavelength by 1 nm from the shortest wavelength within a predetermined wavelength region. For example, the maximum absorbancewithin the wavelength range of 350 nm to 360 nm is the highest absorbanceamong absorbancemeasured at the wavelength of 350 nm, 351 nm, 352 nm, 353 nm, 354 nm, 355 nm, 356 nm, 357 nm, 358 nm, 359 nm and 360 nm.

In the specification, the term "incident angle" used in the present invention is an angle based on normal to a surface to be evaluated. For example, a transmittance at an incident angle of 0° of the optical filter means the transmittance for light incident in a direction parallel to the normal of the optical filter surface. Also, a transmittance at an incident angle of 400 is the transmittance for the incident light forming an angle of 400 in the clockwise or the counter-clockwise direction with respect to the normal of the optical filter surface. This definition of the incident angle is equally applied to other characteristics such as transmittance.

In the specification, the term "alkyl group" means an alkyl group having 1 to 20 carbon numbers, 1 to 16 carbon numbers, 1 to 12 carbon numbers, 1 to 8 carbon numbers, or 1 to 4 carbon numbers. The alkyl group can be straight-chain, branched-chain or cyclic. The alkyl group may optionally be substituted with one or more substituents.

In the specification, the term "alkoxy group" means an alkoxy group having 1 to 20 carbon numbers, 1 to 16 carbon numbers, 1 to 12 carbon numbers, 1 to 8 carbon numbers, or 1 to 4 carbon numbers. The alkoxy group can be straight-chain, branched-chain or cyclic. The alkoxy group may be optionally substituted with one or more substituents.

In the specification, the term "haloalkyl group" refers to an alkyl group substituted with at least one or more halogen elements and the term "alkoxyalkyl group" refers to an alkyl group substituted with at least one or more alkoxy groups. Specific types of alkyl group and alkoxy groups are as described above. In addition, as examples of the halogen atom that may be substituted for the haloalkyl group, fluorine (F), chlorine (C1), bromine (Br), and/or iodine (I) may be exemplified.

The present invention relates to an optical absorbent composition. In the specification, the term "optical absorbent composition" refers to a mixture including two types of optical absorbents having different chemical structures.

The optical absorbent composition, in one example, may include a chemical compound of Chemical Formula 1 and a chemical compound of Chemical Formula 2.

The chemical compounds of Chemical Formulas 1 and 2 have different chemical structures.

[Chemical Formula 1]

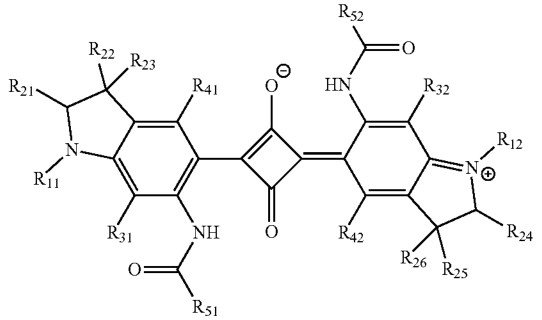

In Chemical Formula 1, $R_{11}$, $R_{12}$, $R_{51}$ and $R_{52}$ may each independently be an alkyl group a haloalkyl group, an alkoxy group or an alkoxyalkyl group $R_{21}$, $R_{22}$, $R_{23}$, $R_{24}$, $R_{25}$, $R_{26}$, $R_{31}$, $R_{32}$, $R_{41}$ and $R_{42}$ may each independently be hydrogen, an alkyl group, an alkoxy group or an alkoxyalkyl group.

[Chemical Formula 2]

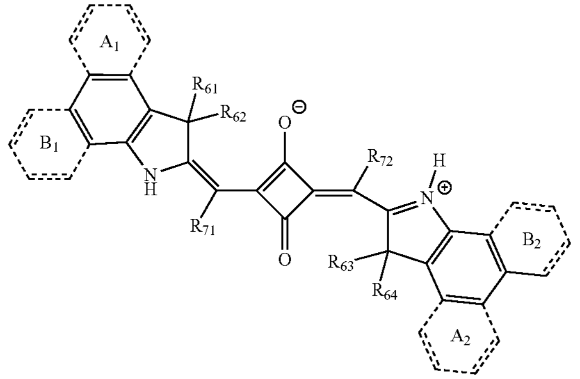

In Chemical Formula 2, $R_{71}$ and $R_{72}$ are each independently an alkyl group, an alkoxy group or an alkoxyalkyl group, $R_{61}$ to $R_{64}$ are each independently hydrogen, an alkyl group, an alkoxy group or an alkoxyalkyl group, and $A_1$, $B_1$, $A_2$ and $B_2$ are each independently a benzene structure or absent.

It is confirmed that an optical absorbent composition constructed by mixing a chemical compound having a frame of Chemical Formula 1 and satisfying any one of Conditions 1 and 2 and a chemical compound having a frame of Chemical Formula 2 and satisfying any one of Conditions 3 and 4 exhibits excellent solubility or compatibility with respect to various solvents and resin components and the optical absorbent composition can provide desired optical properties for an optical absorption film.

In other words, the chemical compound of Chemical Formula 1 satisfies at least one of Conditions 1 and 2:

Condition 1: a sum of carbon numbers of $R_{11}$, $R_{12}$, $R_{51}$, $R_{52}$, $R_{21}$, $R_{22}$, $R_{23}$, $R_{24}$, $R_{25}$, $R_{26}$, $R_{31}$, $R_{32}$, $R_{41}$ and $R_{42}$ in Chemical Formula 1 is 16 or more; and Condition 2: a sum of carbon numbers of $R_{11}$, $R_{12}$, $R_{51}$, $R_{52}$, $R_{21}$, $R_{22}$, $R_{23}$, $R_{24}$, $R_{25}$, $R_{26}$, $R_{31}$, $R_{32}$, $R_{41}$ and $R_{42}$ in Chemical Formula 1 is 14 or more, and at least one of $R_{11}$, $R_{12}$, $R_{51}$, $R_{52}$, $R_{21}$, $R_{22}$, $R_{23}$, $R_{24}$, $R_{25}$, $R_{26}$, $R_{31}$, $R_{32}$, $R_{41}$ and $R_{42}$ is an alkoxy group or an alkoxyalkyl group.

Meanwhile, the chemical compound of Chemical Formula 2 satisfies at least one of Conditions 3 and 4:

Condition 3: a sum of carbon numbers of $R_{61}$, $R_{62}$, $R_{63}$, R 64, $R_{71}$ and $R_{72}$ in Chemical Formula 2 is 10 or more; and Condition 4: a sum of carbon numbers of $R_{61}$, $R_{62}$, $R_{63}$, $R_{64}$, $R_{71}$ and $R_{72}$ is 4 or more, and at least one of $R_{61}$, $R_{62}$, $R_{63}$, $R_{64}$, $R_{71}$, and $R_{72}$ is an alkoxy group or an alkoxyalkyl group in Chemical Formula 2.

For Condition 1, a sum of carbon numbers of $R_{11}$, $R_{12}$, $R_{51}$, $R_{52}$, $R_{21}$, $R_{22}$, $R_{23}$, $R_{24}$, $R_{25}$, $R_{26}$, $R_{31}$, $R_{32}$, $R_{41}$ and $R_{42}$ in Chemical Formula 1 may be 18 or more, 20 or more, 22 or more, 24 or more, 26 or more, 28 or more, or 30 or more. There is no particular limitation on the upper limit of the sum of carbon numbers of $R_{11}$, $R_{12}$, $R_{51}$, $R_{52}$, $R_{21}$, $R_{22}$, $R_{23}$, $R_{24}$, $R_{25}$, $R_{26}$, $R_{31}$, $R_{32}$, $R_{41}$ and $R_{42}$ in Chemical Formula 1 for Condition 1. However, if the sum of the carbon numbers is excessively large, the synthesis of the chemical compound is not easy, the crystallinity of the synthesized chemical compound is deteriorated, and purification may be difficult. Therefore, the sum of the carbon numbers may be, for example, 50 or less, 48 or less, 46 or less, 44 or less, 42 or less, 40 or less, 38 or less, 36 or less, 34 or less, 32 or less, 30 or less, 28 or less, 26 or less, 24 or less or 22 or less.

Even when Condition 1 is satisfied, at least one of $R_{11}$, $R_{12}$, $R_{51}$, $R_{52}$, $R_{21}$, $R_{22}$, $R_{23}$, $R_{24}$, $R_{25}$, $R_{26}$, $R_{31}$, $R_{32}$, $R_{41}$ and $R_{42}$ in Chemical Formula 1 may be an alkoxy group or an alkoxyalkyl group. Although not particularly limited in this case, for example, at least one of $R_{11}$, $R_{12}$, $R_{51}$ and $R_{52}$ may be an alkoxy group or an alkoxyalkyl group.

For Condition 2, a sum of carbon numbers of $R_{11}$, $R_{12}$, $R_{51}$, $R_{52}$, $R_{21}$, $R_{22}$, $R_{23}$, $R_{24}$, $R_{25}$, $R_{26}$, $R_{31}$, $R_{32}$, $R_{41}$ and $R_{42}$ in Chemical Formula 1 may be 14 or more, 16 or more, 18 or more, 20 or more, 22 or more, 24 or more, 26 or more, 28 or more, or 30 or more. There is no particular limitation on the upper limit of the sum of carbon numbers of $R_{11}$, $R_{12}$, $R_{51}$, $R_{52}$, $R_{21}$, $R_{22}$, $R_{23}$, $R_{24}$, $R_{25}$, $R_{26}$, $R_{31}$, $R_{32}$, $R_{41}$ and $R_{42}$ in Chemical Formula 1 for Condition 2. However, if the sum of the carbon numbers is excessively large, the synthesis of the chemical compound is not easy, the crystallinity of the synthesized chemical compound is deteriorated, and purification may be difficult. Therefore, the sum of the carbon numbers may be, for example, about 50 or less, 48 or less, 46 or less, 44 or less, 42 or less, 40 or less, 38 or less, 36 or less, 34 or less, 32 or less, 30 or less, 28 or less, 26 or less, 24 or less, 22 or less, 20 or less, or 18 or less.

For condition 2, especially under Condition 2, if the sum of carbon numbers of $R_{11}$, $R_{12}$, $R_{51}$, $R_{52}$, $R_{21}$, $R_{22}$, $R_{23}$, $R_{24}$, $R_{25}$, $R_{26}$, $R_{31}$, $R_{32}$, $R_{41}$ and $R_{42}$ in Chemical Formula 1 is less than 20, at least one of $R_{11}$, $R_{12}$, $R_{51}$, $R_{52}$, $R_{21}$, $R_{22}$, $R_{23}$, $R_{24}$, $R_{25}$, $R_{26}$, $R_{31}$, $R_{32}$, $R_{41}$ and $R_{42}$ may be an alkoxy group or an alkoxyalkyl group. Although not particularly limited in this case, for example, at least one of $R_{11}$, $R_{12}$, $R_{51}$ and $R_{52}$ may be an alkoxy group or an alkoxyalkyl group.

For Condition 3, a sum of carbon numbers of $R_{61}$, $R_{62}$, $R_{63}$, $R_{64}$, $R_{71}$ and $R_{72}$ in Chemical Formula 2 may be 10 or more, 12 or more, 14 or more, or 16 or more. There is no particular limitation on the upper limit of the sum of carbon numbers of $R_{61}$, $R_{62}$, $R_{63}$, $R_{64}$, $R_{71}$ and $R_{72}$ in Chemical Formula 2 for Condition 3. However, if the sum of the carbon numbers is excessively large, the synthesis of the chemical compound is not easy, the crystallinity of the synthesized chemical compound is deteriorated, and purification may be difficult. Therefore, the sum of the carbon numbers may be, for example, 40 or less, 38 or less, 36 or less, 34 or less, 32 or less, 30 or less, 28 or less, 26 or less, 24 or less, 22 or less, 20 or less, 18 or less, 16 or less, 14 or less, 12 or less, or 10 or less.

Even when Condition 3 is satisfied, at least one of $R_{61}$, $R_{62}$, $R_{63}$, $R_{64}$, $R_{71}$ and $R_{72}$ in Chemical Formula 2 may be an alkoxy group or an alkoxyalkyl group. Although not particularly limited in this case, for example, at least one of $R_{71}$ and $R_{72}$ may be an alkoxy group or an alkoxyalkyl group.

For Condition 4, a sum of carbon numbers of $R_{61}$, $R_{62}$, $R_{63}$, $R_{64}$, $R_{71}$ and $R_{72}$ in Chemical Formula 2 may be 4 or more, 6 or more, 8 or more, 10 or more, 12 or more, 14 or more or 16 or more. There is no particular limitation on the upper limit of the sum of carbon numbers of $R_{61}$, $R_{62}$, $R_{63}$, $R_{64}$, $R_{71}$ and $R_{72}$ in Chemical Formula 2 for Condition 4. However, if the sum of the carbon numbers is excessively large, the synthesis of the chemical compound is not easy, the crystallinity of the synthesized chemical compound is deteriorated, and purification may be difficult. Therefore, the sum of the carbon numbers may be, for example, 40 or less, 38 or less, 36 or less, 34 or less, 32 or less, 30 or less, 28 or less, 26 or less, 24 or less, 22 or less. 20 or less, 18 or less, 16 or less, 14 or less, 12 or less, 10 or less, 8 or less, 6 or less, or 4 or less.

For condition 4, especially under Condition 4, if the sum of carbon numbers of $R_{61}$, $R_{62}$, $R_{63}$, $R_{64}$, $R_{71}$ and $R_{72}$ in Chemical Formula 2 is less than 10, at least one of $R_{61}$, $R_{62}$, $R_{63}$, $R_{64}$, $R_{71}$ and $R_{72}$ in Chemical Formula 2 may be an alkoxy group or an alkoxyalkyl group. Although not particularly limited in this case, for example, at least one of $R_{71}$ and $R_{72}$ may be an alkoxy group or an alkoxyalkyl group.

In Chemical Formula 1, $R_{11}$, $R_{12}$, $R_{51}$ and $R_{52}$ may each independently be an alkyl group, a haloalkyl group, an alkoxy group or an alkoxyalkyl group. The lower limit of the carbon numbers of $R_{11}$, $R_{12}$, $R_{51}$ and $R_{52}$ existing in the alkyl group, the haloalkyl group, the alkoxy group or the alkoxyalkyl group may be 1, 2, 3, 4, 5, 6, 7 or 8 and the upper limit may be 20, 18, 16, 14, 12, 10, 8, 6, 4 or 2. The carbon numbers of $R_{11}$, $R_{12}$, $R_{51}$ and $R_{52}$ existing in the alkyl group, the haloalkyl group, the alkoxy group or the alkoxyalkyl group may be in a range between any one lower limit among the lower limits described above and any one upper limit among the upper limits described above.

The ratio (C1/C5) of the sum of carbon numbers of $R_{11}$ and $R_{12}$ (C1) to the sum of carbon numbers of $R_{51}$ and $R_{52}$ (C5) may be in the range of about 0.1 to 10. In another example, the ratio (C1/C5) may be 0.1 or more, 0.3 or more, 0.5 or more, 1 or more, 1.5 or more, 2 or more, 2.5 or more, or 3 or more or 9 or less, 8 or less, 7 or less, 6 or less, 5 or less, 4 or less, 3 or less, 2 or less, or 1 or less.

In one example, in Chemical Formula 1, the lower limit of the ratio (C11/C12) of the carbon number of $R_1$ (C11) to the carbon number of $R_{12}$ (C12) may be 0.1, 0.3, 0.5, 0.7, 0.9, or 1 and the upper limit may be 2, 1.8, 1.6, 1.4, 1.2 or 1. The ratio (C11/C12) may be in the range between any one of the lower limits described above and any one of the upper limits described above.

In one example, in Chemical Formula 1, the lower limit of the ratio (C51/C52) of the carbon number of $R_{51}$ (C51) to the carbon number of $R_{52}$ (C52) may be 0.1, 0.3, 0.5, 0.7, 0.9 or 1. And, the upper limit may be 2, 1.8, 1.6, 1.4, 1.2 or 1. The ratio (C51/C52) may be in the range between any one of the lower limits described above and any one of the upper limits described above.

In one example of Chemical Formula 1, $R_{21}$, $R_{22}$, $R_{23}$, $R_{24}$, $R_{25}$ and $R_{26}$ may each independently be an alkyl group, an alkoxy group or an alkoxyalkyl group and $R_{31}$, $R_{32}$, $R_{41}$ and $R_{42}$ may be hydrogen. In this case, the carbon numbers of $R_{21}$, $R_{22}$, $R_{23}$, $R_{24}$, $R_{25}$ and $R_{26}$ included in the alkyl group, the alkoxy group or the alkoxyalkyl group may be 1 to 4, 1 to 3, 1 and 2, or 1.

In this case, the lower limit of the ratio (C1/C2) of the sum of the carbon numbers of $R_1$ and $R_{12}$ (C1) to the sum of carbon numbers of $R_{21}$ to $R_{26}$, $R_{31}$, $R_{32}$, $R_{41}$ and $R_{42}$ (C2) in Chemical Formula 1 may be 1, 1.2, 1.4, 1.6, 1.8, or 2, and the upper limit may be 10, 9, 8, 7, 6, 5, 4, 3, 2, or 1.5. The ratio (C1/C2) may be in the range between any one of the lower limits described above and any one of the upper limits described above.

In one example, in Chemical Formula 1, the lower limit of the ratio (CR2/CL2) of the carbon numbers included in $R_{21}$ to $R_{23}$ of (CR2) to the carbon numbers (CL2) included in $R_{24}$ to $R_{26}$ may be 0.1, 0.3, 0.5, 0.7, 0.9 or 1, and the upper limit may be 2, 1.8, 1.6, 1.4, 1.2 or 1. The ratio CR2/CL2 may be in the range between any one of the lower limits described above and any one of the upper limits described above.

In one example, in Chemical Formula 1, the lower limit of the ratio (CR3/CL3) of the carbon number (CR3) included in $R_{31}$ to the carbon number (CL3) included in $R_{32}$ may be 0.1, 0.3, 0.5, 0.7, 0.9 or 1. And, the upper limit may be 2, 1.8, 1.6, 1.4, 1.2 or 1. The ratio CR3/CL3 may be in the range between any one of the lower limits described above and any one of the upper limits described above.

In one example, in Chemical Formula 1, the lower limit of the ratio (CR4/CL4) of the carbon number (CR4) included in $R_{41}$ to the carbon number (CL4) included in $R_{42}$ may be 0.1, 0.3, 0.5, 0.7, 0.9 or 1. And, the upper limit may be 2, 1.8, 1.6, 1.4, 1.2 or 1. The ratio CR4/CL4 may be in the range between any one of the lower limits described above and any one of the upper limits described above.

The alkyl group, the haloalkyl group, the alkoxy group or the alkoxyalkyl group existing in Chemical Formula 1 may each be linear, branched, or cyclic. And it may be optionally substituted with one or more substituents.

In Chemical Formula 2, $R_{71}$ and $R_{72}$ may each independently be an alkyl group, an alkoxy group or an alkoxyalkyl group. The lower limit of the carbon numbers included in the alkyl group, alkoxy group or alkoxyalkyl group of $R_{71}$ and $R_{72}$ may be 1, 2, 3, 4, 5 or 6, and the upper limit may be 20, 18, 16, 14, 12, 10, 8, 6, 4 or 3. The carbon numbers of $R_{71}$ and $R_{72}$ existing in the alkyl group, the alkoxy group or the alkoxyalkyl group may be in the range between any one of the lower limits described above and any one of the upper limits described above.

In one example, in Chemical Formula 2, the lower limit of the ratio (C71/C72) of the carbon number of $R_{71}$ (C71) to the carbon number of $R_{72}$ (C72) may be 0.1, 0.3, 0.5, 0.7, 0.9 or 1 and the upper limit may be 2, 1.8, 1.6, 1.4, 1.2 or 1. The ratio (C71/C72) may be in the range between any one of the lower limits described above and any one of the upper limits described above.

In one example of Chemical Formula 2, $R_{61}$ to $R_{64}$ may each independently be an alkyl group, an alkoxy group or an alkoxyalkyl group. In this case, the carbon numbers included in the alkyl group, the alkoxy group or the alkoxyalkyl group of $R_{61}$ to $R_{64}$ may be 1 to 4, 1 to 3, 1 to 2 or 1.

In this case, the lower limit of the ratio (C7/C6) of the sum of the carbon numbers of $R_{71}$ and $R_{72}$ (C7) to the sum of the carbon numbers of $R_{61}$ to $R_{64}$ (C6) in Chemical Formula 2 may be 0.1, 0.5, 1.5, 2, 2.5 or 3 and the upper limit may be 10, 9, 8, 7, 6, 5, 4, 3, 2 or 1.5. The ratio (C7/C6) may be in the range between any one of the lower limits described above and any one of the upper limits described above.

In one example, the lower limit of the ratio (CR6/CL6) of the carbon numbers included in $R_{61}$ and $R_{62}$ (CR6) in Chemical Formula 2 to the carbon numbers included in $R_{63}$ and $R_{64}$ (CL6) may be 0.1, 0.3, 0.5, 0.7, 0.9 or 1, and the upper limit may be 2, 1.8, 1.6, 1.4, 1.2 or 1. The ratio CR6/CL6 may be in the range between any one of the lower limits described above and any one of the upper limits described above.

The alkyl group, the alkoxy group or the alkoxyalkyl group exisiting in Chemical Formula 2 may be straight chain, branched, or cyclic, respectively. And it may be optionally substituted with one or more substituents.

In Chemical Formula 2, $A_1$, $A_2$, $B_1$ and $B_2$ may each independently have a benzene structure or be absent. The "benzene structure" means that the corresponding dotted line portion is indicated by a solid line, and "absent" means that the corresponding dotted line portion is absent. For example, in Chemical Formula 1, a structure where $A_1$ and $A_2$ are benzene structures and $B_1$ and $B_2$ are absent is represented by Chemical Formula 21.

[Chemical Formula 21]

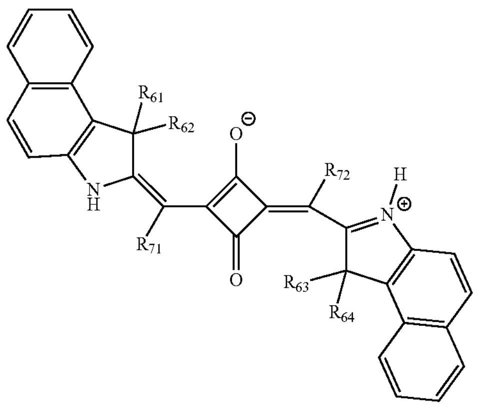

In one example, in Chemical Formula 2, one of $A_1$ and $B_1$ may have a benzene structure and the other may be absent. In Chemical Formula 2, one of $A_2$ and $B_2$ may have a benzene structure and the other may be absent.

To obtain a more appropriate effect, the relationship between Chemical Formula 1 and Chemical Formula 2 may be adjusted. For example, in Chemical Formulas 1 and 2, the upper and/or the lower limits of the sum of the carbon numbers existing in $R_{11}$, $R_{12}$, $R_{51}$, $R_{52}$, $R_{21}$, $R_{22}$, $R_{23}$, $R_{24}$, $R_{25}$, $R_{26}$, $R_{31}$, $R_{32}$, $R_{41}$, $R_{42}$, $R_{61}$, $R_{62}$, $R_{63}$, $R_{64}$, $R_{71}$ and $R_{72}$ may be further adjusted. For example, the lower limit of the sum of the carbon numbers may be 26, 28, 30, 32, 34, 36, 38, 40, 42, 44 or 46. The upper limit of the sum of the carbon numbers may be 80, 75, 70, 65, 60, 55, 50, 48, 46, 44, 42, 40, 38, 36, 34, 32, 30 or 28. The sum of the carbon numbers may be in the range between any one of the lower limits described above and any one of the upper limits described above.

The upper limit and/or lower limit of the ratio (C1/C7) of the sum of the carbon numbers of $R_{11}$ and $R_{12}$ (C1) in Chemical Formula 1 to the sum of the carbon numbers of $R_{71}$ and $R_{72}$ (C7) in Chemical Formula 2 may further be adjusted. For example, the lower limit of the sum of the carbon numbers may be 0.1, 0.3, 0.5, 1, 1.5, or 2. The upper limit of the ratio (C1/C7) may be 10, 9, 8, 7, 6, 5, 4, 3, 2 or 1. The ratio (C1/C7) may be in the range between any one of the lower limits described above and any one of the upper limits described above.

In Chemical Formula 1, the upper and/or the lower limits of the ratio (CA/CB) of the sum of the carbon numbers of $R_{11}$, $R_{12}$, $R_{51}$, $R_{52}$, $R_{21}$, $R_{22}$, $R_{23}$, $R_{24}$, $R_{25}$, $R_{26}$, $R_{31}$, $R_{32}$, $R_{41}$ and $R_{42}$ (CA) to the sum of the carbon numbers of $R_{61}$, $R_{62}$, $R_{63}$, $R_{64}$, $R_{71}$ and $R_{72}$ (CB) may be further adjusted. For example, the lower limit of the sum of the carbon numbers may be 0.5, 0.7, 0.9, 1, 1.1, 1.5, 2 or 2.5. The upper limit of the ratio (CA/CB) may be 5, 4, 3 or 2. The ratio (CA/CB) may be in the range between any one of the lower limits described above and any one of the upper limits described above.

An optical absorbent composition exhibiting desired optical properties can be provided by including the chemical compounds represented by Chemical Formulas 1 and 2. The ratio between the chemical compound of Chemical Formula 1 and the chemical compound of Chemical Formula 2 in the optical absorbent composition is not particularly limited. That is, the ratio between the chemical compound of Chemical Formula 1 and the chemical compound of Chemical Formula 2 may be adjusted in consideration of desired optical properties. In one example, the chemical compound of Chemical Formula 2 may be included in the optical absorbent composition in an amount of about 1 part by weight to 500 parts by weight with respect to 100 parts by weight of the chemical compound of Chemical Formula 1.

In another example, the ratio of the chemical compound of Chemical Formula 2 to 100 parts by weight of the chemical compound of Chemical Formula 1 may be about 5 parts by weight or more, 10 parts by weight or more, 15 parts by weight or more, 20 parts by weight or more, 25 parts by weight or more, 30 parts by weight or more, 35 parts by weight or more, 40 parts by weight or more, 45 parts by weight or more, 50 parts by weight or more, 55 parts by weight or more, 60 parts by weight or more, 65 parts by weight or more, or 70 parts by weight or more or about 450 parts by weight or less, 400 parts by weight 350 parts by weight or less, 300 parts by weight or less, 250 parts by weight or less, 200 parts by weight or less, 150 parts by weight or less, or 100 parts by weight or less. The ratio may be within a range that is less than or equal to any one of the upper limits described above and greater than or equal to any one of the lower limits described above.

To obtain desired effects, the upper and/or the lower limits of the ratio of the chemical compounds represented by Chemical Formulas 1 and 2 for an optical absorbent included in the optical absorbent composition may be adjusted if necessary. For example, the lower limit of the ratio of the total weight of the chemical compounds of Chemical Formulas 1 and 2 with respect to the weight of all optical absorbent components included in the optical absorbent composition may be about 50% by weight, 55% by weight, 60% by weight, 65% by weight, 70% by weight, 75% by weight, 80% by weight, 85% by weight, 90% by weight or 95% by weight. The upper limit of the weight ratio may be about 100% by weight, 95% by weight, 90% by weight or 85% by weight. The ratio may be in the range between any one of the lower limits described above and any one of the upper limits described above.

The optical absorbent composition may contain other components required in addition to the chemical compounds of Chemical Formulas 1 and 2. For example, the optical absorbent composition may further include a resin component serving as a binder. There is no particular limitation on the type of resin component applied in this case. A known resin component may be used to form an optical absorption film, for example, a near-infrared absorption film. In the present invention, the optical absorbent component may exhibit appropriate compatibility or solubility with respect to various known resin components.

Examples of resin components that can be applied may be a cyclo olefin polymer (COP)-base resin, a polyarylate resin, a polysulfone resin, a polyether sulfone resin, a polyparaphenylene resin, a polyarylene ether phosphine oxide resin, a polyimide resin, a polyetherimide resin, a polyamideimide resin, an acrylic resin, a polycarbonate resin, a polyethylene naphthalate resin or a silicone resin, or other various organic resins or one or more of organic-inorganic hybrid base resins, but is limited to.

In the case where the resin component is applied, there is no particular limitation on its ratio. For example, the resin component may be present such that the total weight of the chemical compounds of Chemical Formulas 1 and 2 with respect to 100 parts by weight of the resin component is in the range of about 0.1 to 50 parts by weight.

In another example, the total weight of the chemical compounds of Chemical Formulas 1 and 2 with respect to 100 parts by weight of the resin component may be about 0.5 parts by weight or more, 1 part by weight or more, 1.5 parts by weight or more, 2 parts by weight or more, 2.5 parts by weight or more, 3 parts by weight or more, 3.5 parts by weight or more, 4 parts by weight or more, 4.5 parts by weight or more, 5 parts by weight or more, 5.5 parts by weight or more, 6 parts by weight or more, 6.5 parts by weight or more, or 7 parts by weight or more or about 45 parts by weight or less, 40 parts by weight or less, 35 parts by weight or less, 30 parts by weight or less, 25 parts by weight or less, 20 parts by weight or less, 15 parts by weight or less, or 10 parts by weight or less. The ratio may be within a range that is less than or equal to any one of the upper limits and greater than or equal to any one of the lower limits.

In case where the resin component is applied, the weight ratio of the chemical compound of Chemical Formula 1 with respect to 100 parts by weight of the resin component may be in the range of about 0.5 to 50 parts by weight. The weight ratio of the chemical compound of Chemical Formula 1 with respect to 100 parts by weight of the resin component may be, in another example, about 1 part by weight or more, 1.5 parts by weight or more, 2 parts by weight or more, 2.5 parts by weight or more, 3 parts by weight or more, 3.5 parts by weight or more, 4 parts by weight or more, 4.5 parts by weight or more, 5 parts by weight or more, 5.5 parts by weight or more, 6 parts by weight or more, 6.5 parts by weight or more, or 7 parts by weight or more or about 45 parts by weight or less, 40 parts by weight or less, 35 parts by weight or less 30 parts by weight or less, 25 parts by weight or less, 20 parts by weight or less, 15 parts by weight or less, 10 parts by weight or less, 9 parts by weight or less, 8 parts by weight or less, 7 parts by weight or less, 6 parts by weight or less, or 5 parts by weight or less. The ratio may be within a range that is less than or equal to any one of the upper limits described above and greater than or equal to any one of the lower limits described above.

In case where the resin component is applied, the weight ratio of the chemical compound of Chemical Formula 2 with respect to 100 parts by weight of the resin component may be in the range of about 0.5 to 50 parts by weight. The weight ratio of the chemical compound of Chemical Formula 2 with respect to 100 parts by weight of the resin component may be, in another example, about 1 part by weight or more, 1.5 parts by weight or more, 2 parts by weight or more, 2.5 parts by weight or more, 3 parts by weight or more, 3.5 parts by weight or more, 4 parts by weight or more, 4.5 parts by weight or more, 5 parts by weight or more, 5.5 parts by weight or more, 6 parts by weight or more, 6.5 parts by weight or more, or 7 parts by weight or more or about 45 parts by weight or less, 40 parts by weight or less, 35 parts by weight or less, 30 parts by weight or less, 25 parts by weight or less, 20 parts by weight or less, 15 parts by weight or less, 10 parts by weight or less, 9 parts by weight or less, 8 parts by weight or less, 7 parts by weight or less, 6 parts by weight or less, 5 parts by weight or less, 4 parts by weight or less, or 3 parts by weight or less. The ratio may be within a range that is less than or equal to any one of the upper limits described above and greater than or equal to any one of the lower limits described above.

For example, the optical absorbent composition may further include a solvent in which the absorbent component including the chemical compounds of Chemical Formulas 1 and 2 and/or the resin component are dispersed. There is no particular limitation on the type of solvent applied in this case. A known solvent may be used to form an optical absorption film, for example, a near-infrared absorption film. In the present invention, the optical absorbent component may exhibit appropriate compatibility or solubility with respect to various known solvents.

Examples of the solvent may include, but are not limited to, cyclohexanone, toluene, methyl ethyl ketone, methyl isobutyl ketone, chlorobenzene, or xylene. In case where the solvent is applied, the ratio is not particularly limited, and the ratio may be adjusted within a range in which the chemical compounds of Chemical Formulas 1 and 2 can be properly dispersed.

The optical absorbent composition may contain other necessary components in addition to the components described above.

The present invention also relates to applications of the optical absorbent composition. For example, the present invention relates to an optical absorption film where the optical absorbent composition is applied. The optical absorption film may include at least a resin component and an optical absorbent composition or a chemical compound of Chemical Formula 1 and a chemical compound of Chemical Formula 2. In this case, the specific type of the resin component and the ratio between the resin component and the chemical compounds of Chemical Formulas 1 and 2 are the same as those described for the optical absorbent composition.

The optical absorption film may be a film capable of absorbing light within a predetermined range of wavelengths. In one example, the optical absorption film may be an infrared ray absorbing film or a near infrared ray absorbing film. Such an optical absorption film may exhibit absorption characteristics in at least a portion of a wavelength range of, for example, a wavelength range of 600 nm to 900 nm.

In one example, the optical absorption film may have a relatively wide bandwidth within the wavelength range of 600 nm to 900 nm by using the optical absorbent composition or the chemical compounds of Chemical Formulas 1 and 2. It may have absorption characteristics for longer wavelengths.

Due to these characteristics, the optical absorption film can be applied to a device such as various optical filters or infrared sensors to prevent a shift phenomenon with respect to an incident angle. In addition, when a dielectric film is applied to the optical filter or the infrared sensor, it is possible to prevent defects such as petal flare by adjusting the reflection characteristics of the dielectric film. Moreover, by reducing the number of layers of the dielectric film, advantages for the manufacturing process can be secured.

Accordingly, in one example, the optical absorption film may exhibit an absorption band having a bandwidth of about 60 nm or more within a wavelength range of 600 nm to 900 nm. The absorption band may refer to a region exhibiting a transmittance of about 70% or less in a transmittance curve of the optical absorption film. In addition, the bandwidth means the difference between the longest wavelength exhibiting about 20% transmittance and the shortest wavelength exhibiting about 20% transmittance in the wavelength range of 600 nm to 900 nm of the transmittance curve of the optical absorption film.

In another example, the bandwidth of the optical absorption film within the wavelength range of 600 nm to 900 nm may be about 70 nm or more, 80 nm or more, 90 nm or more, 100 nm or more or 120 nm or more. There is no particular limitation on the upper limit of the bandwidth. For example, the upper limit of the bandwidth may be about 600 nm or less, 550 nm or less, 500 nm or less, 450 nm or less, 400 nm or less, 350 nm or less, 300 nm or less, 250 nm or less, 200 nm or less, 190 nm or less, 180 nm or less, 160 nm or less, 150 nm or less, 140 nm or less or 130 nm or less. The bandwidth may be either greater than or equal to any one of the lower limits or greater than or equal to any one of the lower limits described above and less than or equal to any one of the upper limits described above.

Furthermore, the optical absorption film may have T50% cut-on wavelength within a range of 600 nm to 800 nm. In another example, the lower limit of the T50% cut-on wavelength may be about 610 nm, 620 nm or 630 nm and the upper limit may be about 750 nm, 700 nm, or 650 nm. The T50% cut-on wavelength may be in a range of greater than or equal to any one of the lower limits described above and less than or equal to any one of the upper limits described above. The T50% cut-on wavelength means the shortest wavelength showing a transmittance of 50% in a wavelength range of 600 nm to 900 nm of the transmittance curve of the optical absorption film.

The optical absorption film may have T50% cut-off wavelength in a range of 700 nm to 900 nm. The T50% cut-off wavelength may be a longer wavelength than the T50% cut-on wavelength. The lower limit of the T50% cut-off wavelength may be about 720 nm, 740 nm, 760 nm, 780 nm or 800 nm and the upper limit may be about 880 nm, 860 nm, 840 nm, 820 nm, 810 nm, or 800 nm in another example. The T50% cut-off wavelength may be within a range of greater than or equal to any one of the lower limits described above and less than or equal to any one of the upper limits described above. The T50% cut-off wavelength means the longest wavelength showing transmittance of 50% in the wavelength range of 600 nm to 900 nm of the transmittance curve of the optical absorption film. Through the absorption characteristics, the optical absorption film can be applied to devices such as various optical filters or infrared sensors to efficiently achieve desired characteristics.

The optical absorption film may be formed in a known manner as long as the optical absorbent composition of the present invention is applied. For example, the optical absorption film may be formed by coating the optical absorbent composition in an appropriate manner and, if necessary, performing a curing or drying process.

There is no particular limitation on the thickness of the optical absorption film, and the thickness of the optical absorption film may be adjusted in consideration of desired characteristics. In one example, the optical absorption film may have a thickness of about 0.1 m to about 20 m.

The present invention also relates to an optical filter. The optical filter may include a substrate and the optical absorption film formed on one or both surfaces of the substrate layer.

FIG. 1 is a schematic showing an example of the optical filter where the optical absorption film 200 is formed on one surface of a substrate 100. The optical filter of the present invention may exhibit excellent performance by including the optical absorption film described above. For example, the optical filter efficiently and accurately may block unnecessary infrared ray while implementing a visible light transmission band with high transmittance.

The type of transparent substrate applied to the optical filter is not particularly limited, and a known transparent substrate for an optical filter may be used. In one example, the substrate may be a so-called infrared absorbing substrate. The infrared absorbing substrate is a substrate that exhibits absorption characteristics in at least a portion of the infrared region. A so-called blue glass, which contains copper and exhibits the above characteristics, is a representative example of the infrared absorbing substrate. Such an infrared absorbing substrate is useful in constructing an optical filter that blocks light in the infrared region but is disadvantageous in securing high transmittance in the visible region due to the absorption characteristics and disadvantageous in terms of durability. In the present invention, by selecting an infrared absorbing substrate and combining it with the specific optical absorption film, it is possible to provide an optical filter that efficiently blocks desired light, exhibits high transmittance characteristics in the visible light region, and has excellent durability.

For the infrared absorbing substrate, a substrate exhibiting an average transmittance of 75% or more within a wavelength range of 425 nm to 560 nm may be used. The average transmittance may be within the range of about 77% or more, 79% or more, 81% or more, 83% or more, 85% or more, 87% or more or 89% or more and/or about 98% or less, 96% or less, 94% or less, 92% or less or 90% or less in another example.

For the infrared absorbing substrate, a substrate exhibiting a maximum transmittance of 80% or more within a wavelength range of 425 nm to 560 nm may be used. The maximum transmittance may be within the range of about 82% or more, 84% or more, 86% or more, 88% or more or 90% or more and/or about 100% or less, 98% or less, 96% or less, 94% or less, 92% or less or 90% or less in another example.

For the infrared absorbing substrate, a substrate exhibiting an average transmittance of 75% or more within a wavelength range of 350 nm to 390 nm may be used. The average transmittance may be within the range of about 77% or more, 79% or more, 81% or more or 83% or more and/or about 98% or less, 96% or less, 94% or less, 92% or less, 90% or less, 88% or less, 86% or less or 84% or less in another example.

For the infrared absorbing substrate, a substrate exhibiting a maximum transmittance of 80% or more within a wavelength range of 350 nm to 390 nm may be used. The maximum transmittance may be within the range of about 82% or more, 84% or more, 86% or more or 87% or more and/or about 100% or less, 98% or less, 96% or less, 94% or less, 92% or less, 90% or less or 88% or less in another example.

For the infrared absorbing substrate, a substrate having a transmittance at a wavelength of 700 nm in a range of 10% to 45% may be used. In another example, the transmittance may be within the range of about 43% or less, 41% or less, 39% or less, 37% or less, 35% or less, 33% or less, 31% or less, or 29% or less or about 12% or more, 14% or more, 16% or more, 18% or more, 20% or more, 22% or more, 24% or more, 26% or more, or 28% or more.

For the infrared absorbing substrate, a substrate exhibiting an average transmittance within a range of 5% to 30% within a wavelength range of 700 nm to 800 nm may be used. In another example, the average transmittance may be within the range of about 7% or more, 9% or more, 11% or more, 13% or more, 15% or more, 15.5% or more, 16% or more, or 16.5% or more, and/or about 28% or less, 26% or less, 24% or less, 22% or less, 20% or less, 18% or less or 17% or less.

For the infrared absorbing substrate, a substrate exhibiting a maximum transmittance within a range of 10% to 45% within a wavelength range of 700 nm to 800 nm may be used. The maximum transmittance may be within the range of about 12% or more, 14% or more, 16% or more, 18% or more, 20% or more, 22% or more, 24% or more, 26% or more or 28% or more and/or about 43% or less, 41% or less, 39% or less, 37% or less, 35% or less, 33% or less, 31% or less or 29% or less in another example.

For the infrared absorbing substrate, a substrate exhibiting an average transmittance within a range of 3% to 20% within a wavelength range of 800 nm to 1,000 nm can be used. The average transmittance may be further adjusted within the range of about 5% or more, 7% or more, 9% or more or 11% or more and/or about 18% or less, 16% or less, 14% or less or 12% or less in another example.

For the infrared absorbing substrate, a substrate exhibiting maximum transmittance within a range of 5% to 30% within a wavelength range of 800 nm to 1,000 nm may be used. In another example, the maximum transmittance may within the range of about 7% or more, 9% or more, 11% or more, 13% or more, or 15% or more, and/or about 28% or less, 26% or less, 24% or less, 22% or less, 20% or less, 18% or less or 16% or less.

For the infrared absorbing substrate, a substrate exhibiting an average transmittance within a range of 10% to 50% within a wavelength range of 1,000 nm to 1,200 nm may be used. In another example, the average transmittance may be further adjusted within the range of about 12% or more, 14% or more, 16% or more, 18% or more, 20% or more, 22% or more, 24% or more or 25% or more and/or about 48% or less, 46% or less, 44% or less, 42% or less, 40% or less, 38% or less, 36% or less, 34% or less, 32% or less, 30% or less, 28% or less, or 26% or less.

The infrared absorbing substrate may have a transmission band exhibiting maximum transmittance within a range of 10% to 70% within a wavelength range of 1,000 nm to 1,200 nm. In another example, the maximum transmittance may be about 12% or more, 14% or more, 16% or more, 18% or more, 20% or more, 22% or more, 24% or more, 26% or more, 28% or more, 30% or more, 32% or more, 34% or more or 36% or more and/or about 68% or less, 66% or less, 64% or less, 62% or less, 60% or less, 58% or less, 56% or less, 54% or less, 52% or less, 50% or less, 48% or less, 46% or less, 44% or less, 42% or less, 40% or less, 38% or less or 37% or less.

The infrared absorbing substrate having the above characteristics can be combined with the optical absorption film of the present invention to construct a desired optical filter. As such a substrate, a substrate known as a so-called infrared absorbing glass can be used. Such glass is an absorption-type glass manufactured by adding CuO or the like to a fluorophosphate-based glass or a phosphate-based glass. Therefore, in one example in the present invention, for the infrared absorbing substrate, a CuO-containing fluorophosphate glass substrate or a CuO-containing phosphate glass substrate may be used. The phosphate glass includes a silicophosphate glass where a part of the frame of the glass is composed of $SiO_2$. Such absorption-type glass is known, and for example, a glass disclosed in Korean Patent Registration No. 10-2056613 or other commercially available absorption-type glass (e.g., commercially available products made by such as Hoya Co., Schott Co., or PTOT Co.) may be used.

This infrared absorbing substrate contains copper. In the present invention, a substrate where the copper content is in the range of about 1 wt % to 7 wt % may be used. In another example, the copper content may be about 1.5 wt % or more, 2 wt % or more, 2.5 wt % or more, 2.6 wt % or more, 2.7 wt % or more, or 2.8 wt % or more or about 6.5 wt % or less, 6 wt % or less, or 5.5 wt % or less, 5 wt % or less, 4.5 wt % or less, 4 wt % or less, 3.5 wt % or less, 3 wt % or less, or 2.9 wt % or less. A substrate having such a copper content tends to exhibit the above-mentioned optical properties and it can form an optical filter having desired properties in combination with the above optical absorption film.

The copper content can be confirmed by using an X-ray fluorescence analysis equipment (WD XRF, Wavelength Dispersive X-Ray Fluorescence Spectrometry). When X-rays are irradiated on a specimen (a substrate) using the equipment, characteristic secondary X-rays are generated from individual elements of the specimen and the equipment detects the secondary X-rays according to the wavelength of each element. The intensity of the secondary X-rays is proportional to the element content, and therefore, quantitative analysis can be performed through the intensity of the secondary X-rays measured according to the wavelength of each element.

The thickness of the infrared absorbing substrate may be adjusted within a range of, for example, about 0.03 mm to about 5 mm, but is not limited to.

The optical filter of the present invention may include other known components required in addition to the substrate and the optical absorption film. For example, the optical filter may further include a dielectric film. The optical filter, for example, may further include a so-called dielectric film on one side or both sides of the substrate.

Figure 2:
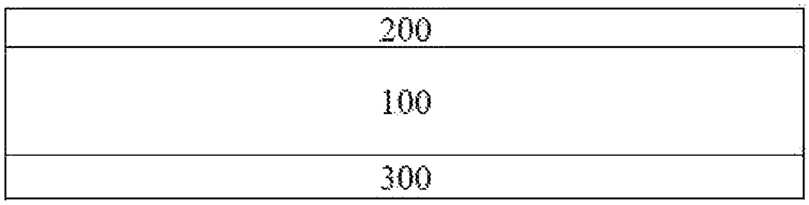
Figure 3:
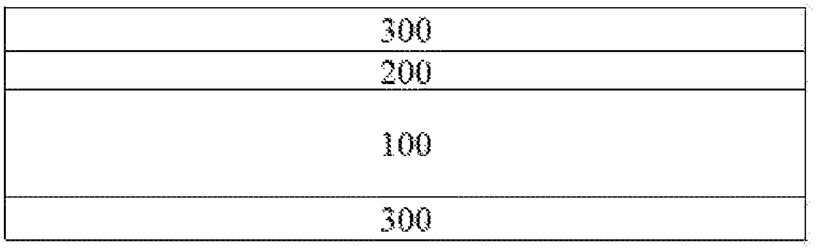

FIGS. 2 and 3 disclose examples of an optical filter to which a dielectric film 300 is added. The schematics disclose an example where the dielectric film 300 is formed on one or both sides of a stacked structure including a substrate 100 and an optical absorption film 200.

This dielectric film is a film formed by repeatedly stacking a dielectric material with a low refractive index and a dielectric material with a high refractive index and is used to form a so-called IR reflective layer and an anti-reflection (AR) layer. In the present invention, a dielectric film for forming such a known IR reflective layer or an AR layer may be applied.

Consequently, the dielectric film may be a multilayer structure including at least two sublayers of each having a different refractive index and may include a multilayer structure where the two sublayers are repeatedly stacked.

The type of material forming the dielectric film, that is, the material forming each of the sub-layers, is not particularly limited, and known material may be applied. In general, $SiO_2$ or fluorides such as $Na_5Al_3Fl_4$, $Na_3AlF_6$ or $MgF_2$ may be used to manufacture the low refractive index sublayer, and amorphous silicon, $TiO_2$, $Ta_2O_5$, $Nb_2O_5$, ZnS or ZnSe, etc. may be used to manufacture the high refractive index sublayer, but material applied in the present invention is not limited to.

A method of forming the dielectric film as described above is not particularly limited and the dielectric film may be formed, for example, by applying a known deposition method. In the industry, a method for controlling reflection or transmission characteristics of a corresponding dielectric film in consideration of the deposition thickness or number of layers of a sublayer is known, and in the present invention, the dielectric film may be formed according to such a known method.

In one example, in the dielectric film included in the optical filter of the present invention, the shortest wavelength exhibiting a reflectance of 50% within a wavelength range of 600 nm to 900 nm may be about 710 nm or more, or such wavelength may not exist. In addition, the maximum reflectance of the dielectric film is less than 50% in the wavelength range of 600 nm to 900 nm when the above wavelength is absent. The shortest wavelength exhibiting the 50% reflectance, if present, in another example, may be about 715 nm or more, 720 nm or more, 725 nm or more, 730 nm or more, 735 nm or more, 740 nm or more, 745 nm or more, 750 nm or more, or 754 nm or more or about 900 nm or less, 850 nm or less, 800 nm or less, 790 nm or less, 780 nm or less, 770 nm or less, or 760 nm or less. The shortest wavelength exhibiting a reflectance of 50% may be within a range between a lower limit of any of the lower limits described above and an upper limit, and in this case, the upper limit may be 900 nm.

As described above, by controlling the reflection characteristics of the dielectric film, so-called petal flare phenomenon can be prevented. The petal flare phenomenon refers to a phenomenon where red lines, which are not observed with the naked eye, are shown in a picture when photographing a luminous body. It is called as a petal flare because the red lines are often shaped like petals on the luminous body. As the sensitivity of the sensor included in the image capturing device increases and the transmittance of the optical filter is increased to obtain a clearer picture, the frequency of the occurrence of the petal flare phenomenon is increasing.

One of the causation of the petal flare phenomenon may be that reflection of near-infrared ray is repeated within an image capturing device equipped with an optical filter. Since a so-called IR film among dielectric films formed in a conventional optical filter is formed to block light in the near-infrared region by reflection, the shortest wavelength at which the dielectric film exhibits a reflectance of 50% is formed near visible light which is usually less than 710 nm. However, reflection of near-infrared ray is accelerated in the image capturing device by such a dielectric film, and thus the petal flare phenomenon occurs. However, when the shortest wavelength where the dielectric film exhibits 50% reflectance is adjusted to about 710 nm or more, the infrared ray blocking efficiency of the optical filter is deteriorated.

However, infrared ray can be effectively blocked even when the shortest wavelength at which the dielectric film exhibits a reflectance of 50% is adjusted to about 710 nm or more through the optical absorption film in the present invention, and the petal flare can also be prevented. A design method itself for controlling the reflection characteristics of a dielectric film is known.

The optical filter may further include an optical absorption film (referred to as an ultraviolet absorption film) exhibiting ultraviolet absorbing characteristics as an optical absorption film distinct from the optical absorption film. However, such an optical absorption film is not an essential component, and for example, an ultraviolet absorbent described later may be incorporated into one optical absorption film together with the chemical compounds of Chemical Formulas 1 and 2.

In one example, the UV absorption film may be designed to exhibit an absorption maximum in a wavelength range of about 300 nm to 390 nm.

The UV absorption film may include only an UV absorbent and it may include two or more kinds of UV absorbents if necessary. For example, as the ultraviolet absorbent, a known absorbent exhibiting an absorption maximum in a wavelength range of about 300 nm to 390 nm can be applied, and examples thereof include ABS 407 manufactured by Exiton; UV381A, UV381B, UV382A, UV386A, VIS404A from QCR Solutions Co.; ADA1225, ADA3209, ADA3216, ADA3217, ADA3218, ADA3230, ADA5205, ADA3217, ADA2055, ADA6798, ADA3102, ADA3204, ADA3210, ADA2041, ADA3201, ADA3202, ADA3215, ADA3219, ADA3225, ADA3232, ADA4160, ADA5278, ADA5762, ADA6826, ADA7226, ADA4634, ADA3213, ADA3227, ADA5922, ADA5950, ADA6752, ADA7130, ADA8212, ADA2984, ADA2999, ADA3220, ADA3228, ADA3235, ADA3240, ADA3211, ADA3221, ADA5220, ADA7158 from HW Sands Co.; and DLS 381B, DLS 381C, DLS 382A, DLS 386A, DLS 404A, DLS 405A, DLS 405C, DLS 403A from CRYSTALYN Co., but are not limited to.

Material and construction methods constituting the ultraviolet absorption film are not particularly limited and known material and construction methods may be applied.

Usually, an UV absorption film is formed by using material in which an UV absorbent capable of exhibiting a desired absorption maximum and a transparent resin are blended. In this case, a resin component applied to the optical absorbent composition may be applied as the transparent resin.

In addition to the above-described layers, necessary various layers may be added to the optical filter within a scope that does not impair the desired effect.

The present invention also relates to an image capturing device including the optical filter. At this time, a configuration method of the image capturing device, or an application method of the optical filter is not particularly limited, and known configuration and application methods may be applied.

In addition, the application of the optical filter of the present invention is not limited to the image capturing device and it can be applied to various other applications requiring near-infrared ray cut (e.g., a display device such as a PDP).

The present invention also relates to an infrared sensor including the optical absorption film. The configuration of the infrared sensor is not particularly limited as long as the optical absorption film of the present invention is included. For example, a known motion sensor, a proximity sensor, or a gesture sensor may be configured by introducing the optical absorption film of the present invention.

In addition, the application of an optical absorbent composition or an optical absorption film in the present invention is not limited to the optical filter, the infrared sensor, and/or the image capturing device. The optical absorbent composition or the optical absorption film can be applied to various other applications requiring infrared ray cut (e.g., a display device such as a PDP).

An optical filter of the present invention will be specifically described through the following embodiments, but the scope of the optical filter of the present invention is not limited by the following embodiments.

1. Evaluation of Transmittance Spectrum

The transmittance spectrum was measured by using a spectrophotometer (Manufacturer: Perkinelmer Co., Product Name: Lambda 750 Spectrophotometer) for a specimen obtained by cutting the measurement subject (e.g., an optical absorption film) to 10 mm and 10 mm in width and length, respectively. The transmittance spectrum was measured for each wavelength and incident angle according to the manual of the equipment. The specimen was placed on a straight line between the measuring beam and the detector of the spectrophotometer, and the transmittance spectrum was checked while changing the incident angle of the measuring beam from 0° to 40°. Unless specifically stated otherwise, the result of the transmittance spectrum in this embodiment was the result when the incident angle is 0°. The incident angle of 0° is a direction substantially parallel to the direction normal to the surface of the specimen.

The average transmittance within a predetermined wavelength region in the transmittance spectrum was the result of measuring the transmittance of each wavelength while increasing the wavelength by 1 nm from the shortest wavelength in the wavelength region, and then calculating the arithmetic average of the measured transmittance. The maximum transmittance is the maximum one among the transmittance measured while increasing the wavelength by 1 nm. For example, the average transmittance within the wavelength range of 350 nm to 360 nm is the arithmetic average of transmittances measured at wavelengths of 350 nm, 351 nm, 352 nm, 353 nm, 354 nm, 355 nm, 356 nm, 357 nm, 358 nm, 359 nm and 360 nm and the maximum transmittance within the wavelength range of 350 nm to 360 nm is the highest transmittance among transmittances measured at wavelengths of 350 nm, 351 nm, 352 nm, 353 nm, 354 nm, 355 nm, 356 nm, 357 nm, 358 nm, 359 nm and 360 nm.

2. Mass Analysis

Mass analysis of the synthesized chemical compound was performed using a liquid chromatograph/mass spectrometer (manufactured by Thermo Finnigan).

Synthesis Example 1. Preparation of Chemical Compound ($A_1$)

The chemical compound of Chemical Formula $A_1$ was synthesized through the process of Chemical Reaction Formula 1.

[Chemical Reaction Formula 1]

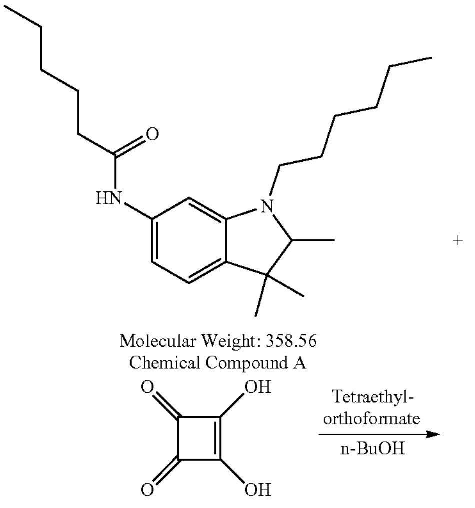

Molecular Weight: 358.56
Chemical Compound A
Squaric acid

-continued

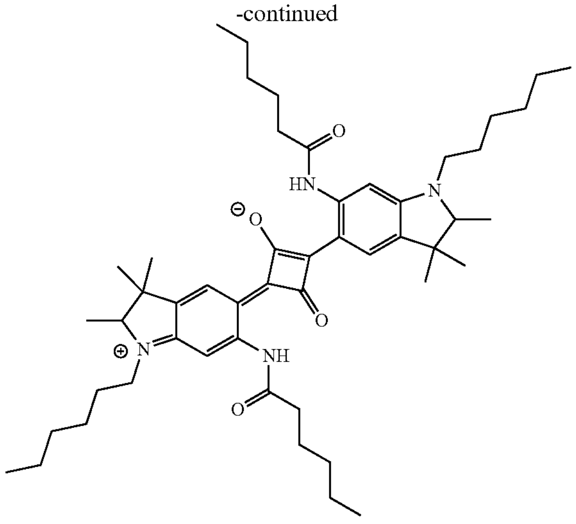

Molecular Weight: 795.15
Chemical Compound A1

14.1 g of Chemical Compound A of Chemical Reaction Formula 1, 2.24 g of Squaric acid and 8.7 g of tetraethyl orthoformate is dissolved in 100 mL of n-butanol and reacted at 95° C. for about 4 hours. After completion of the reaction, cool to room temperature (about 25° C.), add 300 mL of ethanol, and stir for 6 hours or more. Then, precipitated solids were filtered under reduced pressure while passing ethanol to obtain the desired product (chemical compound of Chemical Formula A1) (7.4 g, 51%). Mass analysis results for the synthesized desired chemical compound (chemical compound of Chemical Formula A1) are as follows:

<Mass Analysis Result>

LC-MS m/z 739.7 $[M+H]^+$

Synthesis Example 2. Preparation of Chemical Compound (A2)

The chemical compound of Chemical Formula A2 was synthesized through the process of Chemical Reaction Formula 2.

[Chemical Reaction Formula 2]

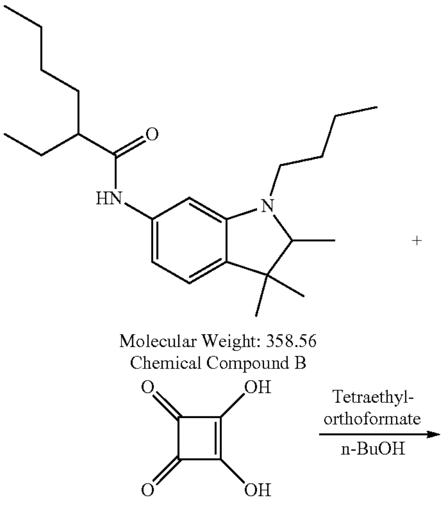

Molecular Weight: 358.56
Chemical Compound B
Squaric acid

-continued

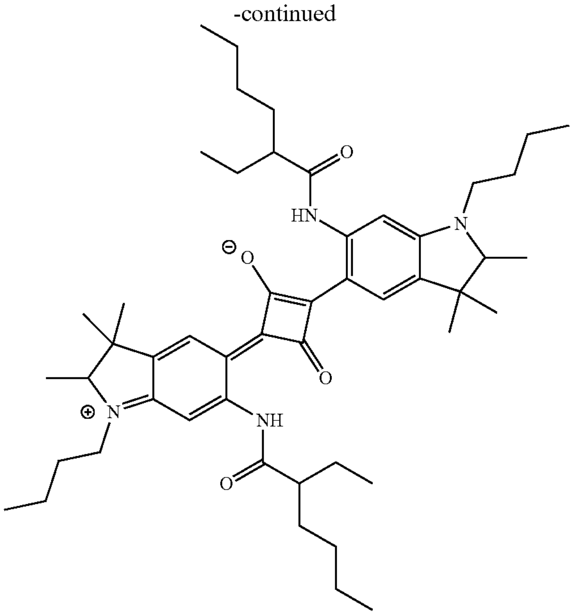

Molecular Weight: 795.15
Chemical Compound A2

14.1 g of Chemical Compound B of Chemical Reaction Formula 2, 2.24 g of squaric acid and 8.7 g of tetraethyl orthoformate was dissolved in 100 mL of n-butanol and reacted at 95° C. for about 4 hours. After completion of the reaction, cool to room temperature (about 25° C.), add 300 mL of ethanol, and stir for 6 hours or more. Then, precipitated solids were filtered under reduced pressure while passing ethanol to obtain the desired product (chemical compound of Chemical Formula A2) (6.1 g, 39%). Mass analysis results for the synthesized desired chemical compound (chemical compound of Chemical Formula A2) are as follows:

<Mass Analysis Result>

LC-MS m/z 795.7 $[M+H]^+$

Synthesis Example 3. Preparation of Chemical Compound A3

The chemical compound of Chemical Formula A3 was synthesized through the process of Chemical Reaction Formula 3.

[Chemical Reaction Formula 3]

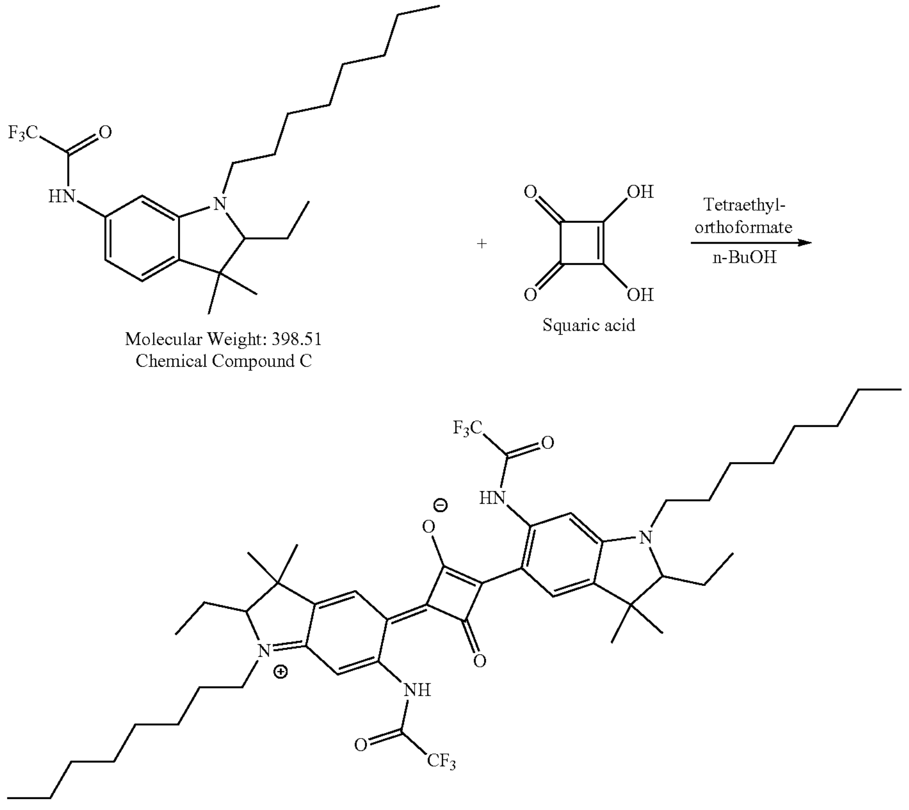

Molecular Weight: 398.51
Chemical Compound C

Squaric acid

Molecular Weight: 875.04
Chemical Compound A3

17.5 g of Chemical Compound C of Chemical Reaction Formula 3, 2.5 g of squaric acid and 9.8 g of tetraethyl orthoformate was dissolved in 100 mL of n-butanol and reacted at 95° C. for about 4 hours. After completion of the reaction, cool to room temperature (about 25° C.), add 300 mL of ethanol, and stir for 6 hours or more. Then, precipitated solids were filtered under reduced pressure while passing ethanol to obtain the desired product (chemical compound of Chemical Formula A3) (6.9 g, 36%). Mass analysis results for the synthesized desired chemical compound (chemical compound of Chemical Formula A3) are as follows:

<Mass Analysis Result>

LC-MS m/z 876.1 $[M+H]^+$

Synthesis Example 4. Preparation of Chemical Compound (A4)

The chemical compound of Chemical Formula A4 was synthesized through the process of Chemical Reaction Formula 4.

[Chemical Reaction Formula 4]

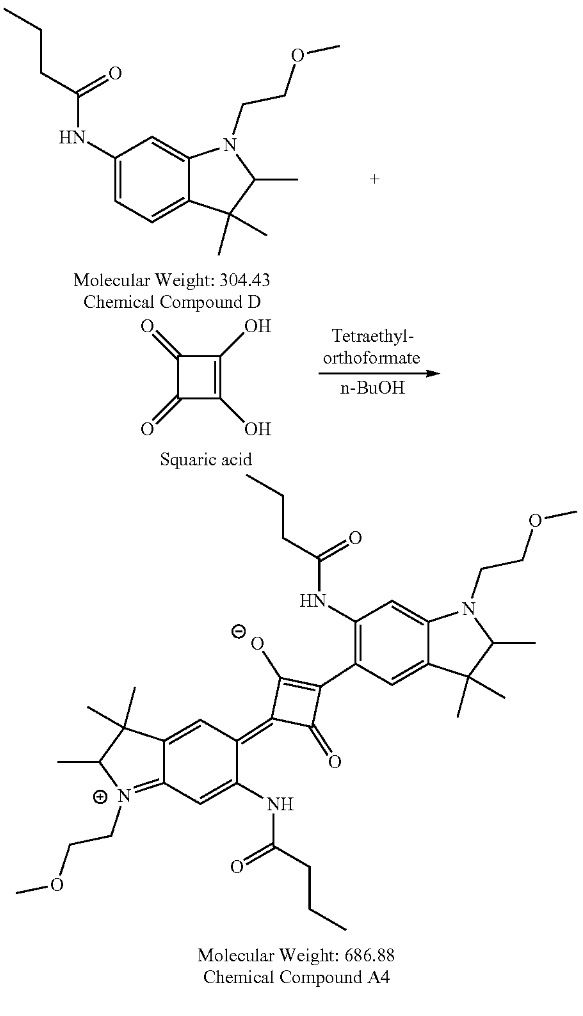

14 g of Chemical Compound D of Chemical Reaction Formula 4, 2.5 g of squaric acid, and 9.3 g of tetraethyl orthoformate was dissolved in 100 mL of n-butanol and reacted at 95° C. for about 4 hours. After completion of the reaction, cool to room temperature (about 25° C.), add 300 mL of ethanol, and stir for 6 hours or more. Then, precipitated solids were filtered under reduced pressure while passing ethanol to obtain the desired product (chemical compound of Chemical Formula A4) (6.8 g, 45%). Mass analysis results for the synthesized desired chemical compound (chemical compound of Chemical Formula A4) are as follows:

<Mass Analysis Result>

LC-MS m/z 687.5 $[M+H]^+$

Synthesis Example 5. Preparation of Chemical Compound (A5)

The chemical compound of Chemical Formula A5 was synthesized through the process of Chemical Reaction Formula 5.

[Chemical Reaction Formula 5]

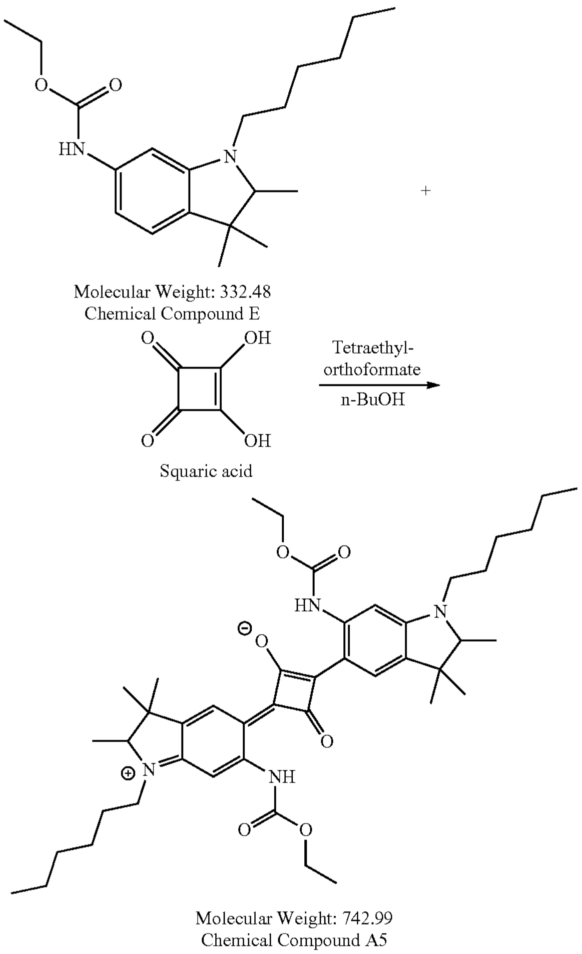

15.3 g of Chemical Compound E of Chemical Reaction Formula 5, 2.5 g of squaric acid, and 9.8 g of tetraethyl orthoformate was dissolved in 100 mL of n-butanol and reacted at 95° C. for about 4 hours. After completion of the reaction, cool to room temperature (about 25° C.), add 300 mL of ethanol, and stir for 6 hours or more. Then, precipitated solids were filtered under reduced pressure while passing ethanol to obtain the desired product (chemical compound of Chemical Formula A5) (7.2 g, 44%). Mass analysis results for the synthesized desired chemical compound (chemical compound of Chemical Formula A5) are as follows:

<Mass Analysis Result>

LC-MS m/z 743.6 $[M+H]^+$

Synthesis Example 6. Preparation of Chemical Compound (A6)

The chemical compound of Chemical Formula A6 was synthesized through the process of Chemical Reaction Formula 6.

[Chemical Reaction Formula 6]

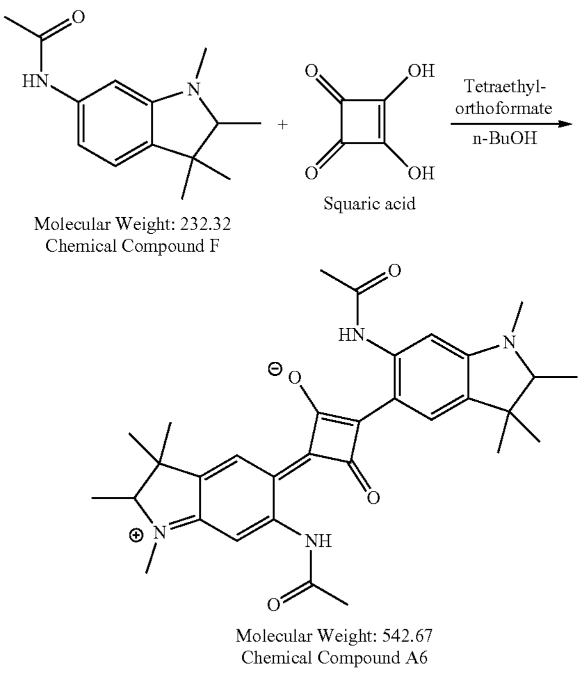

10.7 g of Chemical Compound F of Chemical Reaction Formula 6, 2.5 g of squaric acid, and 9.3 g of tetraethyl orthoformate was dissolved in 100 mL of n-butanol and reacted at 95° C. for about 4 hours. After completion of the reaction, cool to room temperature (about 25° C.), add 300 mL of ethanol, and stir for 6 hours or more. Then, precipitated solids were filtered under reduced pressure while passing ethanol to obtain the desired product (chemical compound of Chemical Formula A6) (5.7 g, 48%). Mass analysis results for the synthesized desired chemical compound (chemical compound of Chemical Formula A6) are as follows:

<Mass Analysis Result>

LC-MS m/z 543.4 $[M+H]^+$

Synthesis Example 7. Preparation of Chemical Compound ($B_1$)

The chemical compound of Chemical Formula $B_1$ was synthesized through the process of Chemical Reaction Formula 7.

[Chemical Reaction Formula 7]

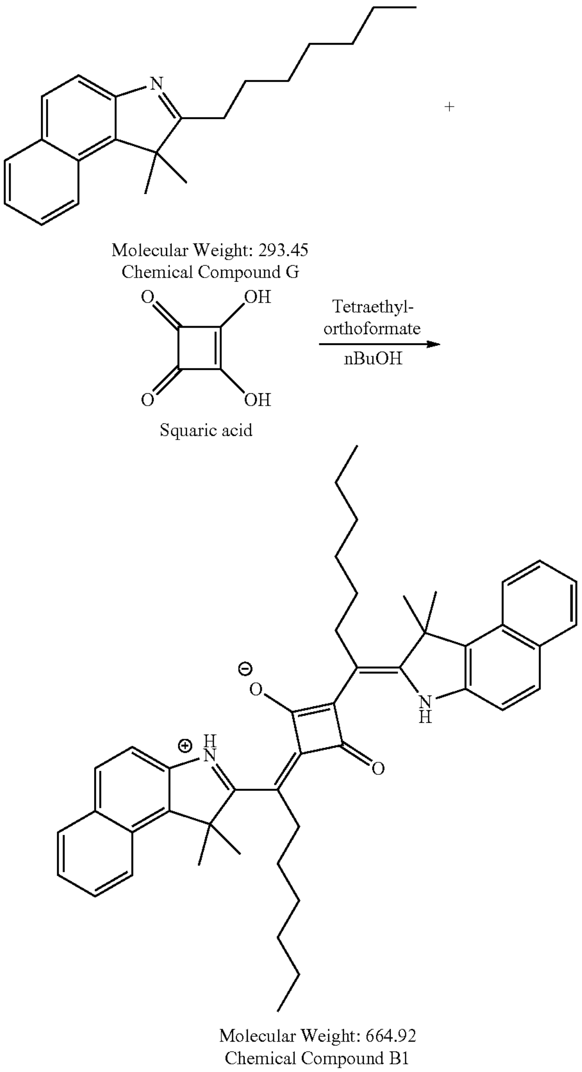

10.1 g of Chemical Compound G of Chemical Reaction Formula 7, 2.0 g of squaric acid, and 7.8 g of tetraethyl orthoformate was dissolved in 100 mL of n-butanol and reacted at 95° C. for about 4 hours. After completion of the reaction, cool to room temperature (about 25° C.), add 300 mL of ethanol, and stir for 6 hours or more. Then, precipitated solids were filtered under reduced pressure while passing ethanol to obtain the desired product (chemical compound of Chemical Formula B1) (6.8 g, 58%). Mass analysis results for the synthesized desired chemical compound (chemical compound of Chemical Formula B1) are as follows:

<Mass Analysis Result>

LC-MS m/z 665.8 $[M+H]^+$

Synthesis Example 8. Preparation of Chemical Compound (B2)

The chemical compound of Chemical Formula B2 was synthesized through the process of Chemical Reaction Formula 8.

[Chemical Reaction Formula 8]

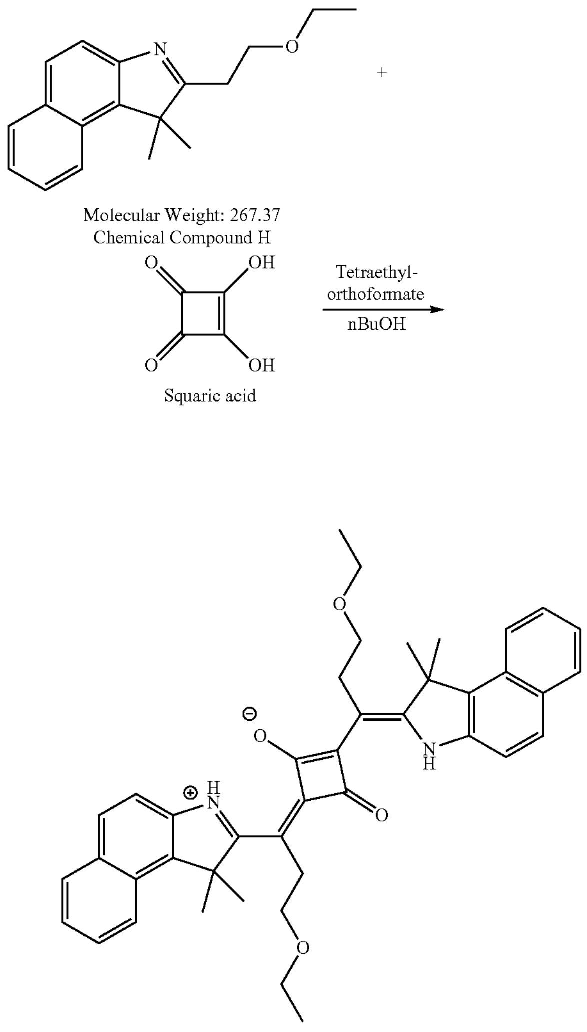

Molecular Weight: 267.37
Chemical Compound H

Squaric acid

Molecular Weight: 640.81
Chemical Compound B2

8.9 g of Chemical Compound H of Chemical Reaction Formula 8, 2.0 g of squaric acid, and 7.5 g of tetraethyl orthoformate was dissolved in 100 mL of n-butanol and reacted at 95° C. for about 4 hours. After completion of the reaction, cool to room temperature (about 25° C.), add 300 mL of ethanol, and stir for 6 hours or more. Then, precipitated solids were filtered under reduced pressure while passing ethanol to obtain the desired product (chemical compound of Chemical Formula B2) (5.9 g, 55%). Mass analysis results for the synthesized desired chemical compound (chemical compound of Chemical Formula B2) are as follows:

<Mass Analysis Result>

LC-MS m/z 641.5 $[M+H]^+$

Synthesis Example 9. Preparation of Chemical Compound (B3)

The chemical compound of Chemical Formula B3 was synthesized through the process of Chemical Reaction Formula 9.

[Chemical Reaction Formula 9]

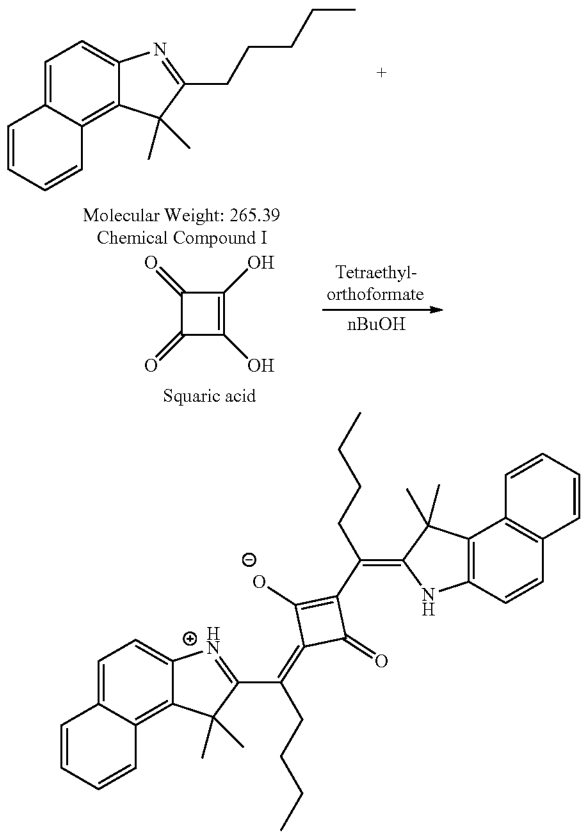

Molecular Weight: 265.39
Chemical Compound I

Squaric acid

Molecular Weight: 606.81
Chemical Compound B3

8.8 g of Chemical Compound I of Chemical Reaction Formula 9, 2.0 g of squaric acid, and 7.8 g of tetraethyl orthoformate was dissolved in 100 mL of n-butanol and reacted at 95° C. for about 4 hours. After completion of the reaction, cool to room temperature (about 25° C.), add 300 mL of ethanol, and stir for 6 hours or more. Then, precipitated solids were filtered under reduced pressure while passing ethanol to obtain the desired product (chemical compound of Chemical Formula B3) (5.4 g, 51%). Mass analysis results for the synthesized desired chemical compound (chemical compound of Chemical Formula B3) are as follows:

<Mass Analysis Result>

LC-MS m/z 609.2 $[M+H]^+$

Synthesis Example 10. Preparation of Chemical Compound (B4)

The chemical compound of Chemical Formula B4 was synthesized through the process of Chemical Reaction Formula 10.

[Chemical Reaction Formula 10]

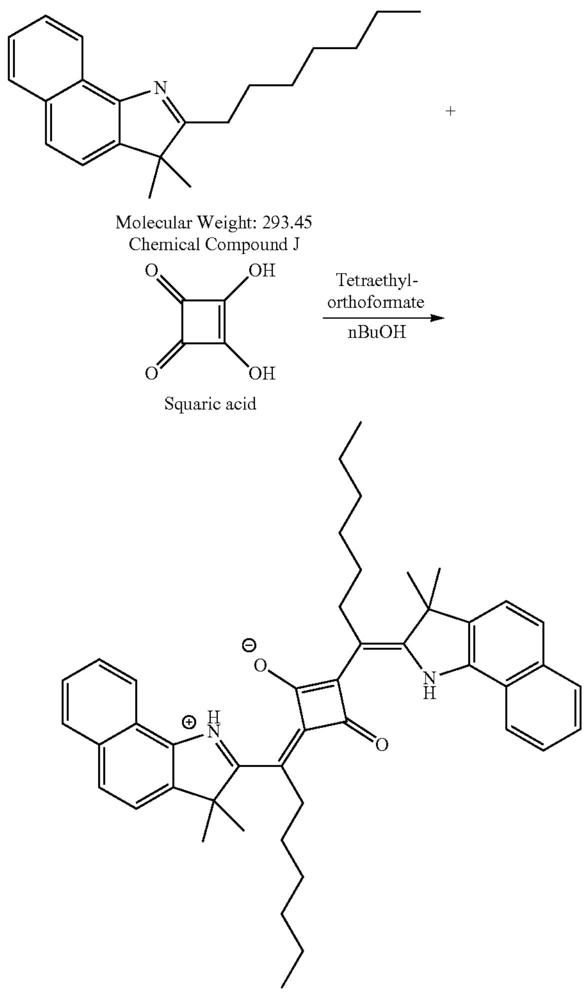

Molecular Weight: 664.92
Chemical Compound B4

10.3 g of Chemical Compound J of Chemical Reaction Formula 10, 2.0 g of squaric acid, and 8.5 g of tetraethyl orthoformate was dissolved in 100 mL of n-butanol and reacted at 95° C. for about 4 hours. After completion of the reaction, cool to room temperature (about 25° C.), add 300 mL of ethanol, and stir for 6 hours or more. Then, precipitated solids were filtered under reduced pressure while passing ethanol to obtain the desired product (chemical compound of Chemical Formula B4) (3.6 g, 31%). Mass analysis results for the synthesized desired chemical compound (chemical compound of Chemical Formula B4) are as follows:

<Mass Analysis Result>

LC-MS m/z 665.4 $[M+H]^+$

Synthesis Example 11. Preparation of Chemical Compound (B5)

The chemical compound of Chemical Formula B5 was synthesized through the process of Chemical Reaction Formula 11.

[Chemical Reaction Formula 11]

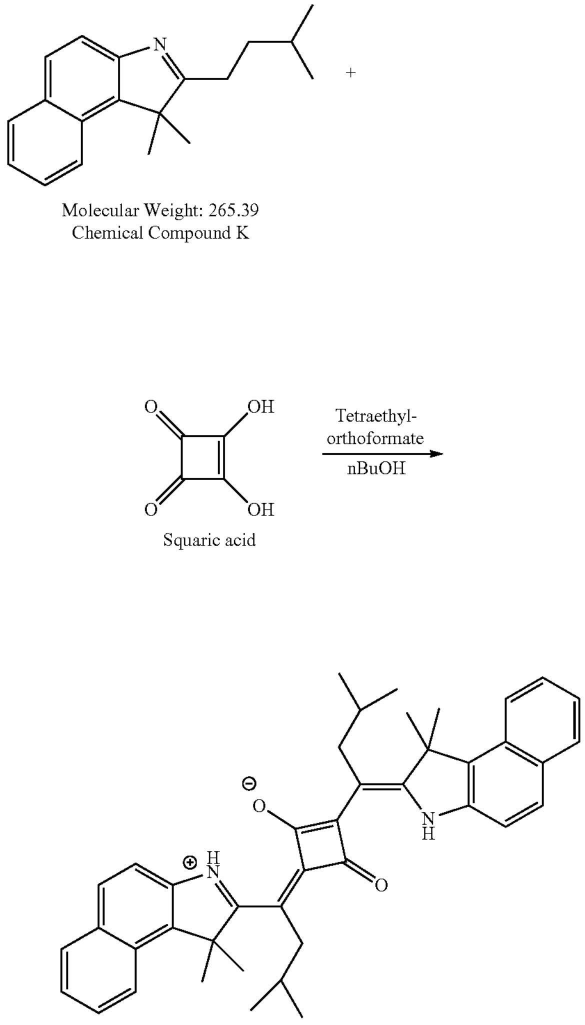

Molecular Weight: 608.81
Chemical Compound B5

9.3 g of Chemical Compound K of Chemical Reaction Formula 11, 2.0 g of squaric acid, and 7.8 g of tetraethyl orthoformate was dissolved in 100 mL of n-butanol and reacted at 95° C. for about 4 hours. After completion of the reaction, cool to room temperature (about 25° C.), add 300 mL of ethanol, and stir for 6 hours or more. Then, precipitated solids were filtered under reduced pressure while passing ethanol to obtain the desired product (chemical compound of Chemical Formula B5) (5.7 g, 53%). Mass analysis results for the synthesized desired chemical compound (chemical compound of Chemical Formula B5) are as follows:

<Mass Analysis Result>

LC-MS m/z 636.4 $[M+H]^+$

Synthesis Example 12. Preparation of Chemical Compound (B6)

The chemical compound of Chemical Formula B6 was synthesized through the process of Chemical Reaction Formula 12.

[Chemical Reaction Formula 12]

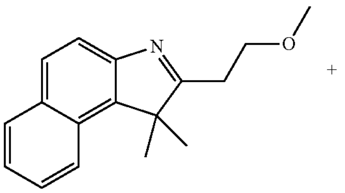

Molecular Weight: 253.34
Chemical Compound L

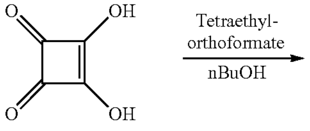

Squaric acid

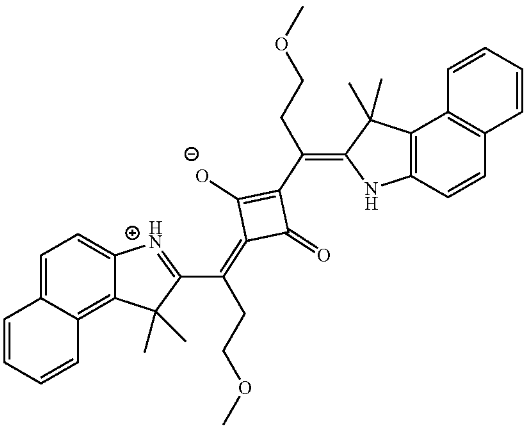

Molecular Weight: 612.76
Chemical Compound B6

8.9 g of Chemical Compound L of Chemical Reaction Formula 12, 2.0 g of squaric acid, and 7.8 g of tetraethyl orthoformate was dissolved in 100 mL of n-butanol and reacted at 95° C. for about 4 hours. After completion of the reaction, cool to room temperature (about 25° C.), add 300 mL of ethanol, and stir for 6 hours or more. Then, precipitated solids were filtered under reduced pressure while passing ethanol to obtain the desired product (chemical compound of Chemical Formula B6) (5.6 g, 52%). Mass analysis results for the synthesized desired chemical compound (chemical compound of Chemical Formula B6) are as follows:

<Mass Analysis Result>

LC-MS m/z 612.3 $[M+H]^+$

Synthesis Example 13. Preparation of Chemical Compound (B7)

The chemical compound of Chemical Formula B7 was synthesized through the process of Chemical Reaction Formula 13.

[Chemical Reaction Formula 13]

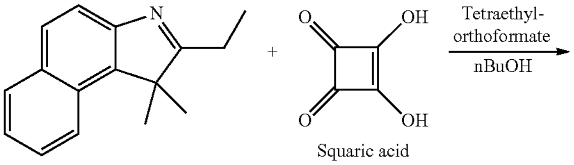

Molecular Weight: 223.31
Chemical Compound M

Squaric acid

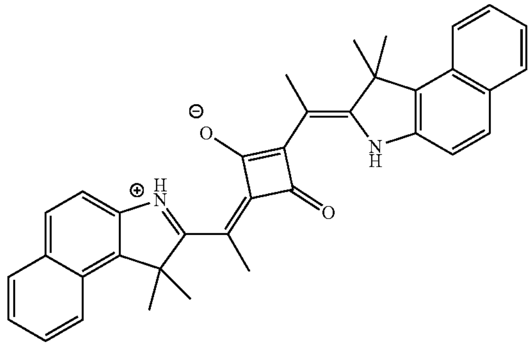

Molecular Weight: 524.65
Chemical Compound B7

7.8 g of Chemical Compound M of Chemical Reaction Formula 13, 2.0 g of squaric acid, and 7.8 g of tetraethyl orthoformate was dissolved in 100 mL of n-butanol and reacted at 95° C. for about 4 hours. After completion of the reaction, cool to room temperature (about 25° C.), add 300 mL of ethanol, and stir for 6 hours or more. Then, precipitated solids were filtered under reduced pressure while passing ethanol to obtain the desired product (chemical compound of Chemical Formula B7) (4.5 g, 49%). Mass analysis results for the synthesized desired chemical compound (chemical compound of Chemical Formula B7) are as follows:

<Mass Analysis Result>

LC-MS m/z 525.6 $[M+H]^+$

Synthesis Example 14. Preparation of Chemical Compound (B8)

The chemical compound of Chemical Formula B8 was synthesized through the process of Chemical Reaction Formula 14.

[Chemical Reaction Formula 14]

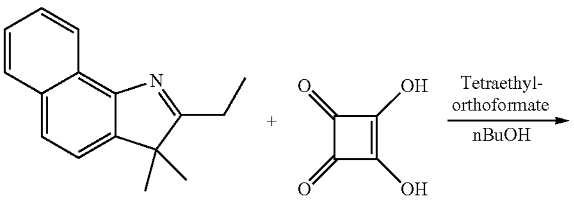

Molecular Weight: 223.31
Chemical Compound N

Squaric acid

-continued

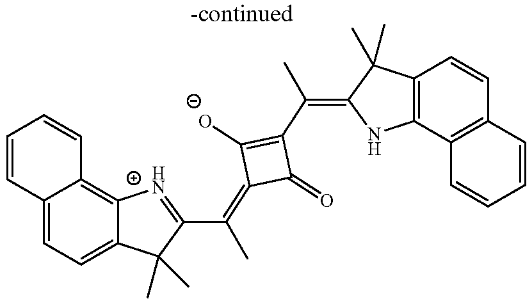

Molecular Weight: 524.65
Chemical Compound B8

7.8 g of Chemical Compound N of Chemical Reaction Formula 14, 2.0 g of squaric acid, and 7.8 g of tetraethyl orthoformate was dissolved in 100 mL of n-butanol and reacted at 95° C. for about 4 hours. After completion of the reaction, cool to room temperature (about 25° C.), add 300 mL of ethanol, and stir for 6 hours or more. Then, precipitated solids were filtered under reduced pressure while passing ethanol to obtain the desired product (chemical compound of Chemical Formula B8) (3.9 g, 42%). Mass analysis results for the synthesized desired chemical compound (chemical compound of Chemical Formula B8) are as follows:

<Mass Analysis Result>

LC-MS m/z 525.5 $[M+H]^+$

The solubility of each synthesized chemical compound was evaluated. Solubility was determined according to the following criteria by evaluating the solubility of each chemical compound in a plurality of solvents (cyclohexanone, toluene, methyl isobutyl ketone (MIBK) or methyl ethyl ketone (MEK)) at room temperature (about 25° C.).

<Solubility Criteria>

A: When the solubility is 1% by mass or more.

B: When the solubility is 0.5% by mass or more and less than 1% by mass.

C: When the solubility is 0.2% by mass or more and less than 0.5% by mass.

D: When the solubility is less than 0.2% by mass.

The solubility evaluation results were summarized and described in Table 1.

TABLE 1

| | Cyclohexanone | Toluene | MIBK | MEK |
|---|---|---|---|---|
| Synthesis Example 1 | A | A | A | A |
| Synthesis Example 2 | A | A | A | A |
| Synthesis Example 3 | A | A | A | A |
| Synthesis Example 4 | A | A | A | A |
| Synthesis Example 5 | A | A | A | A |
| Synthesis Example 6 | B | B | B | B |
| Synthesis Example 7 | A | B | A | A |
| Synthesis Example 8 | A | A | A | A |
| Synthesis Example 9 | A | B | B | B |
| Synthesis Example 10 | A | A | A | A |
| Synthesis Example 11 | A | B | A | A |
| Synthesis Example 12 | A | A | A | A |
| Synthesis Example 13 | D | D | D | C |
| Synthesis Example 14 | C | D | D | C |

Embodiment 1

An optical absorbent composition was prepared by dispersing the chemical compound of Synthesis Example 1 (Chemical Formula A1) and the chemical compound of Synthesis Example 7 (Chemical Formula B1) in a mixture containing a solvent and a resin component at a weight ratio (A1:B1) of about 55:40. In the above process, the dispersion was such that the total weight of the chemical compound of Synthesis Example 1 and Synthesis Example 7 was about 7 parts by weight relative to 100 parts by weight of the resin component.

A mixture where LG Chem's acrylic resin (polymethylmethacrylate) (PMMA) is dispersed in methyl isobutyl ketone (MIBK) at a concentration of about 15% by weight (Embodiment 1-1), a mixture where silicone resin (Dow Co.) is dispersed in cyclohexanone at a concentration of about 15% by weight (Embodiment 1-2), or a mixture where a cyclo olefin polymer (COP)-base resin (TOPAS Co.) is dispersed in cyclohexanone at a concentration of about 15% by weight (Embodiment 1-3) was applied as the mixture of the resin component and the solvent.

Embodiment 2

An optical absorbent composition was prepared in the same manner as in Embodiment 1, except that the chemical compound of Synthesis Example 2 (Chemical Formula A2) was used instead of the chemical compound of Synthesis Example 1 (Chemical Formula A1). As the mixture of the resin component and the solvent, the same mixture of acrylic resin (PMMA (polymethylmethacrylate)) and methyl isobutyl ketone (MIBK) (Embodiment 2-1), mixture of silicone resin and cyclohexanone (Embodiment Example 2-2) or mixture of cyclo olefin polymer (COP)-base resin and cyclohexanone (Embodiment 2-3) as in Embodiment 1 was applied.

Embodiment 3

An optical absorbent composition was prepared in the same manner as in Embodiment 1, except that the chemical compound of Synthesis Example 8 (Chemical Formula B2) was used instead of the chemical compound of Synthesis Example 7 (Chemical Formula B1). As the mixture of the resin component and the solvent, the same mixture of acrylic resin (polymethylmethacrylate (PMMA)) and methyl isobutyl ketone (MIBK) (Embodiment 3-1), mixture of silicone resin and cyclohexanone (Embodiment Example 3-2) or mixture of cyclo olefin polymer (COP)-base resin and cyclohexanone (Embodiment 3-3) as in Embodiment 1 was applied.

Embodiment 4

An optical absorbent composition was prepared in the same manner as in Embodiment 1 except that the chemical compound of Synthesis Example 2 (Chemical Formula A2) was used instead of the chemical compound of Synthesis Example 1 (Chemical Formula A1) and the chemical compound of Synthesis Example 9 (Chemical Formula B3) was used instead of the chemical compound of Synthesis Example 7 (Chemical Formula B1). As the mixture of the resin component and the solvent, the same mixture of acrylic resin (PMMA (polymethylmethacrylate)) and methyl isobutyl ketone (MIBK) (Embodiment 4-1), mixture of silicone resin and cyclohexanone (Embodiment 4-2) or mixture of cyclo olefin polymer (COP)-base resin and cyclohexanone (Embodiment 4-3) as in Embodiment 1 was applied.

Embodiment 5

An optical absorbent composition was prepared in the same manner as in Embodiment 1 except that the chemical compound of Synthesis Example 4 (Chemical Formula A4) was used instead of the chemical compound of Synthesis Example 1 (Chemical Formula A1) and the chemical compound of Synthesis Example 10 (Chemical Formula B4) was used instead of the chemical compound of Synthesis Example 7 (Chemical Formula B1). As the mixture of the resin component and the solvent, the same mixture of the same acrylic resin (PMMA (polymethylmethacrylate)) and methyl isobutyl ketone (MIBK), mixture of silicone resin and cyclohexanone (Embodiment Example 5-2) or mixture of cyclo olefin polymer (COP)-base resin and cyclohexanone (Embodiment 5-3) as in Embodiment 1 was applied.

Embodiment 6

An optical absorbent composition was prepared in the same manner as in Embodiment 1 except that the chemical compound of Synthesis Example 5 (Chemical Formula A5) was used instead of the chemical compound of Synthesis Example 1 (Chemical Formula A1) and the chemical compound of Synthesis Example 11 (Chemical Formula B5) was used instead of the chemical compound of Synthesis Example 7 (Chemical Formula B1). As the mixture of the resin component and the solvent, the same mixture of acrylic resin (PMMA (polymethylmethacrylate)) and methyl isobutyl ketone (MIBK) (Embodiment 6-1), mixture of silicone resin and cyclohexanone (Embodiment 6-2) or mixture of cyclo olefin polymer (COP)-base resin and cyclohexanone (Embodiment 6-3) as in Embodiment 1 was applied.

Embodiment 7

An optical absorbent composition was prepared in the same manner as in Embodiment 1 except that the chemical compound of Synthesis Example 5 (Chemical Formula A5) was used instead of the chemical compound of Synthesis Example 1 (Chemical Formula A1) and the chemical compound of Synthesis Example 8 (Chemical Formula B2) was used instead of the chemical compound of Synthesis Example 7 (Chemical Formula B1). As the mixture of the resin component and the solvent, the same mixture of acrylic resin (PMMA (polymethylmethacrylate)) and methyl isobutyl ketone (MIBK (Embodiment 7-1), mixture of silicone resin and cyclohexanone (Embodiment 7-2) or mixture of cyclo olefin polymer (COP)-base resin and cyclohexanone (Embodiment 7-3) as in Embodiment 1 was applied.

Embodiment 8

An optical absorbent composition was prepared in the same manner as in Embodiment 1 except that the chemical compound of Synthesis Example 5 (Chemical Formula A5) was used instead of the chemical compound of Synthesis Example 1 (Chemical Formula A1) and the chemical compound of Synthesis Example 12 (Chemical Formula B6) was used instead of the chemical compound of Synthesis Example 7 (Chemical Formula B1). As the mixture of the resin component and the solvent, the same mixture of acrylic resin (PMMA (polymethylmethacrylate)) and methyl isobutyl ketone (MIBK) (Embodiment 8-1), mixture of silicone resin and cyclohexanone (Embodiment 8-2) or mixture of cyclo olefin polymer (COP)-base resin and cyclohexanone (Embodiment 8-3) as in Embodiment 1 was applied.

Embodiment 9

An optical absorbent composition was prepared in the same manner as in Embodiment 1 except that the chemical compound of Synthesis Example 5 (Chemical Formula A5) was used instead of the chemical compound of Synthesis Example 1 (Chemical Formula A1) and the chemical compound of Synthesis Example 9 (Chemical Formula B3) was used instead of the chemical compound of Synthesis Example 7 (Chemical Formula B1). As the mixture of the resin component and the solvent, the same mixture of acrylic resin (PMMA (polymethylmethacrylate)) and methyl isobutyl ketone (MIBK) (Embodiment 9-1), mixture of silicone resin and cyclohexanone (Embodiment 9-2) or mixture of cyclo olefin polymer (COP)-base resin and cyclohexanone (Embodiment 9-3) as in Embodiment 1 was applied.

Comparative Example 1

An optical absorbent composition was prepared in the same manner as in Embodiment 1 except that the chemical compound of Synthesis Example 5 (Chemical Formula A5) was used instead of the chemical compound of Synthesis Example 1 (Chemical Formula A1) and the chemical compound of Synthesis Example 13 (Chemical Formula B7) was used instead of the chemical compound of Synthesis Example 7 (Chemical Formula B1). As the mixture of the resin component and the solvent, the same mixture of acrylic resin (PMMA (polymethylmethacrylate)) and methyl isobutyl ketone (MIBK) (Comparative Example 1-1), mixture of silicone resin and cyclohexanone (Comparative Example 1-2) or mixture of cyclo olefin polymer (COP)-base resin and cyclohexanone (Comparative Example 1-3) as in Embodiment 1 was applied.

Comparative Example 2

An optical absorbent composition was prepared in the same manner as in Embodiment 1 except that the chemical compound of Synthesis Example 6 (Chemical Formula A6) was used instead of the chemical compound of Synthesis Example 1 (Chemical Formula A1). As the mixture of the resin component and the solvent, the same mixture of acrylic resin (PMMA (polymethylmethacrylate)) and methyl isobutyl ketone (MIBK) (Comparative Example 2-1), mixture of silicone resin and cyclohexanone (Comparative Example 2-2) or mixture of cyclo olefin polymer (COP)-base resin and cyclohexanone (Comparative Example 2-3) as in Embodiment 1 was applied.

Comparative Example 3

An optical absorbent composition was prepared in the same manner as in Embodiment 1 except that the chemical compound of Synthesis Example 6 (Chemical Formula A6) was used instead of the chemical compound of Synthesis Example 1 (Chemical Formula A1) and the chemical compound of Synthesis Example 8 (Chemical Formula B2) was used instead of the chemical compound of Synthesis Example 7 (Chemical Formula B1). As the mixture of the resin component and the solvent, the same mixture of acrylic resin (PMMA (polymethylmethacrylate)) and methyl isobutyl ketone (MIBK) (Comparative Example 3-1), mixture of silicone resin and cyclohexanone (Comparative Example 3-2) or mixture of cyclo olefin polymer (COP)-base resin and cyclohexanone (Comparative Example 3-3) as in Embodiment 1 was applied.

Comparative Example 4

An optical absorbent composition was prepared in the same manner as in Embodiment 1 except that the chemical compound of Synthesis Example 6 (Chemical Formula A6) was used instead of the chemical compound of Synthesis Example 1 (Chemical Formula A1) and the chemical compound of Synthesis Example 13 (Chemical Formula B7) was used instead of the chemical compound of Synthesis Example 7 (Chemical Formula B1). As the mixture of the resin component and the solvent, the same mixture of acrylic resin (PMMA (polymethylmethacrylate)) and methyl isobutyl ketone (MIBK) (Comparative Example 4-1), mixture of silicone resin and cyclohexanone (Comparative Example 4-2) or mixture of cyclo olefin polymer (COP)-base resin and cyclohexanone (Comparative Example 4-3) as in Embodiment 1 was applied.

Comparative Example 5

An optical absorbent composition was prepared in the same manner as in Embodiment 1 except that the chemical compound of Synthesis Example 6 (Chemical Formula A6) was used instead of the chemical compound of Synthesis Example 1 (Chemical Formula A1) and the chemical compound of Synthesis Example 14 (Chemical Formula B8) was used instead of the chemical compound of Synthesis Example 7 (Chemical Formula B1). As the mixture of the resin component and the solvent, the same mixture of acrylic resin (PMMA (polymethylmethacrylate)) and methyl isobutyl ketone (MIBK) (Comparative Example 5-1), mixture of silicone resin and cyclohexanone (Comparative Example 5-2) or mixture of cyclo olefin polymer (COP)-base resin and cyclohexanone (Comparative Example 5-3) as in Embodiment 1 was applied.

The solubility of each optical absorbent composition in Embodiments and Comparative Examples was evaluated. Solubility was evaluated according to the following criteria while injecting each optical absorbent composition using a syringe filter having a filter size of about 1 m at room temperature (about 25° C.).

<Solubility Criteria>

A: When the optical absorbent composition passes through the filter well without clogging upon injecting through the syringe filter.

B: When the optical absorbent composition passes through the filter upon injecting through the syringe filter, but the passage speed is remarkably slowed down due to clogging.

C: When the optical absorbent composition does not pass through the filter upon injecting through the syringe filter.

The evaluation results were summarized and described in Table 2. In Table 2, Condition 1 is a case where a mixture of acrylic resin (polymethylmethacrylate (PMMA)) and methyl isobutyl ketone (MIBK) is used, Condition 2 is a case where a mixture of a silicone resin and cyclohexanone is used, and Condition 3 is a case where a mixture of a cyclo olefin polymer (COP)-base resin and cyclohexanone is used as a mixture of the resin component and the solvent of the optical absorbent composition.

TABLE 2

| | Solubility | | |
|---|---|---|---|
| | Condition 1 | Condition 2 | Condition 3 |
| Embodiment 1 | A | A | A |
| Embodiment 2 | A | A | A |
| Embodiment 3 | A | A | A |
| Embodiment 4 | A | A | A |
| Embodiment 5 | A | A | B |
| Embodiment 6 | A | A | B |
| Embodiment 7 | A | A | B |
| Embodiment 8 | A | A | B |
| Embodiment 9 | A | B | B |
| Comparative Example 1 | B | B | C |
| Comparative Example 2 | B | B | C |
| Comparative Example 3 | B | C | C |
| Comparative Example 4 | C | C | C |
| Comparative Example 5 | C | C | C |

Embodiment 10

An optical absorbent composition was prepared by mixing a cyclo olefin polymer (COP), the chemical compound of Synthesis Example 1 (Chemical Formula A1), the chemical compound of Synthesis Example 7 (B1) and the solvent (cyclohexanone) in a weight ratio of 1.5:0.055:0.04:10 (COP:A1: B1: cyclohexanone) and stirring for 12 hours or more. As a result of evaluating the solubility of this composition in the above manner, the evaluation result was "A" (the optical absorbent composition passes through the filter well without clogging upon injection through a syringe filter).

Figure 4:
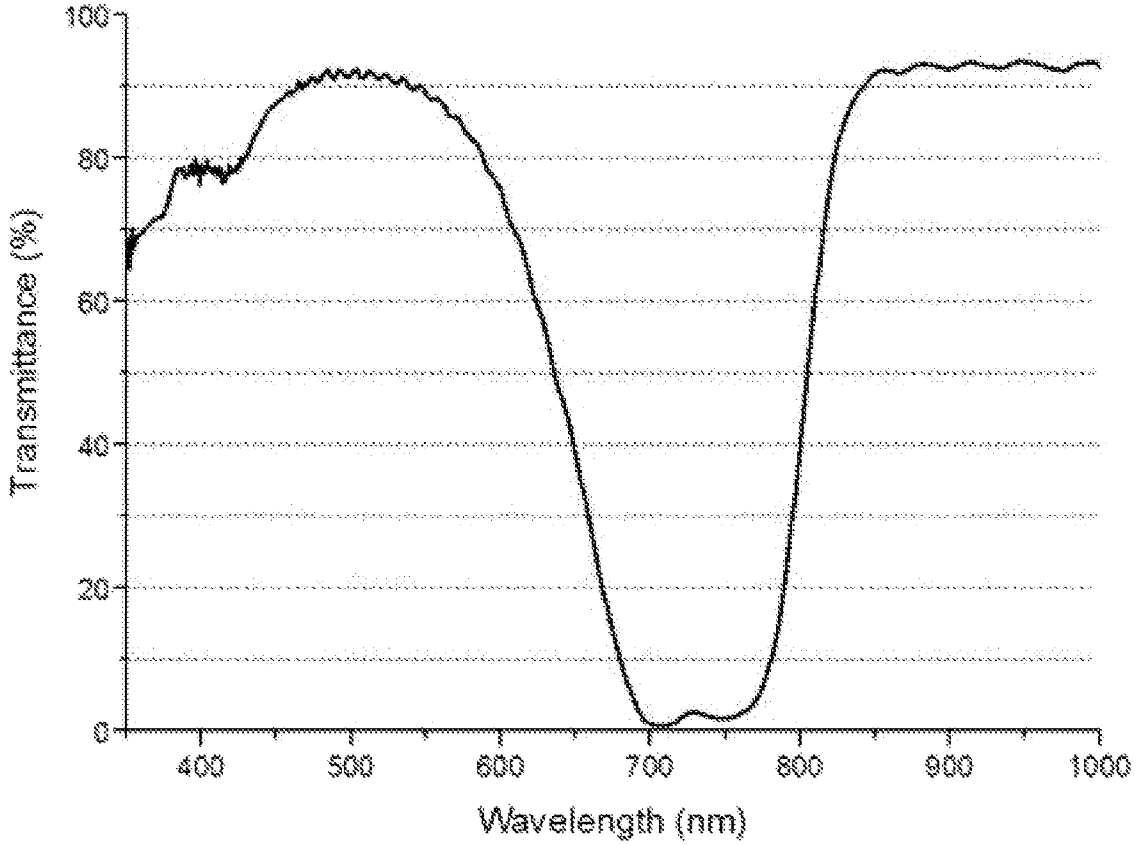
FIGS. 4 to 6 are transmittance spectra showing the evaluation result of optical absorption films prepared in Embodiments or Comparative Examples.

The optical absorbent composition was spin-coated on a transparent substrate (SCHOTT Co., Ltd.) that does not substantially absorb and reflect light. Then, it was heat-treated at a temperature of about 1300 C for about 2 hours to form an optical absorption film having a thickness of about 3 am. FIG. 4 is a spectrum showing the evaluation result of the transmittance of the optical absorption film.

Embodiment 11

An optical absorbent composition was prepared by mixing a silicone resin, the chemical compound of Synthesis Example 2 (Chemical Formula A2), the chemical compound of Synthesis Example 9 (B33) and a solvent (cyclohexanone) in a weight ratio of 1.5:0.055:0.04:10 (silicon resin:A2:B3:cyclohexanone) and stirring for 12 hours or more. As a result of evaluating the solubility of this composition in the above manner, the evaluation result was "A" (the optical absorbent composition passes through the filter well without clogging upon injecting through a syringe filter).

Figure 5:
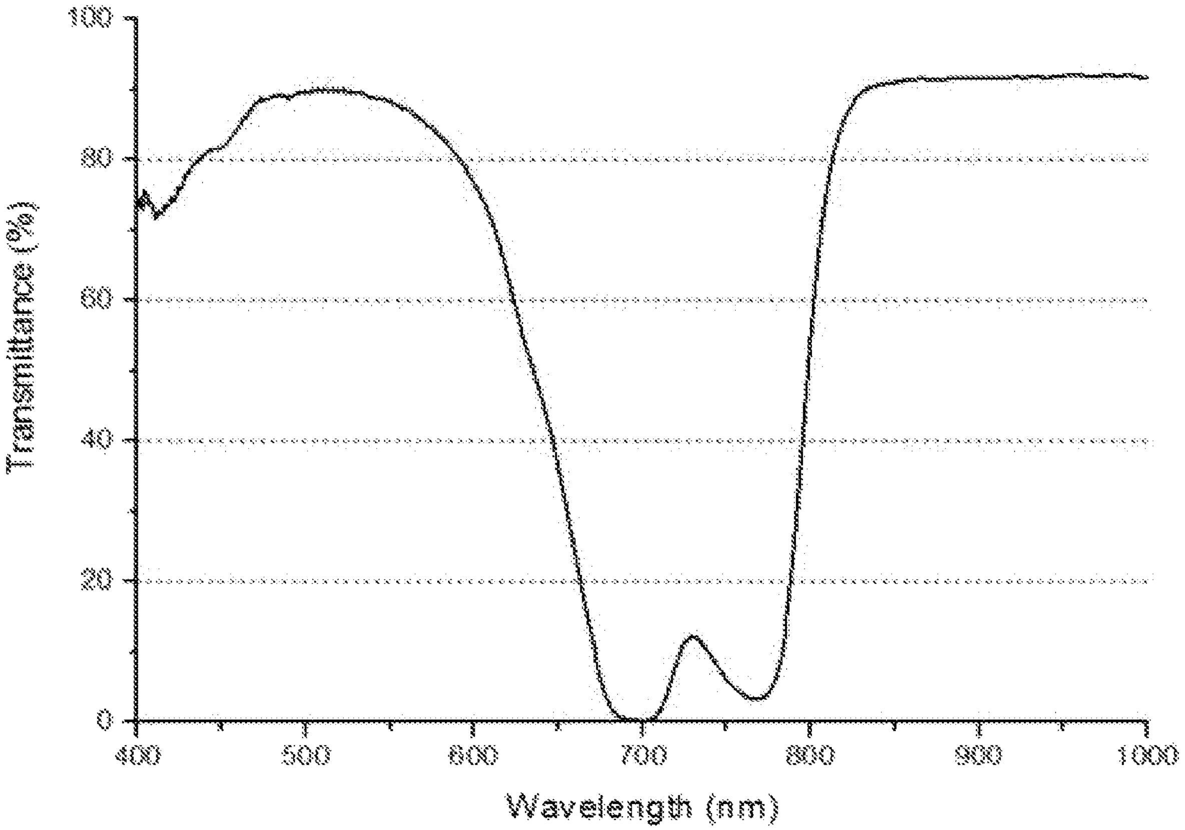

An optical absorption film was formed in the same manner as in Embodiment 10 using the optical absorbent composition. FIG. 5 is a spectrum showing the evaluation result of the transmittance of the optical absorption film.

Comparative Example 6

An optical absorbent composition was prepared by mixing a silicone resin, the chemical compound of Synthesis Example 5 (Chemical Formula A5), the chemical compound of Synthesis Example 13 (B7) and a solvent (cyclohexanone) in a weight ratio of 1.5:0.055:0.04:10 (silicon: A4:B7:cyclohexanone) and stirring for 12 hours or more. As a result of evaluating the solubility of this composition in the above manner, the evaluation result was "B" (the optical absorbent composition passes through the filter upon injecting through the syringe filter, but the passage speed is remarkably slow due to clogging).

Figure 6:
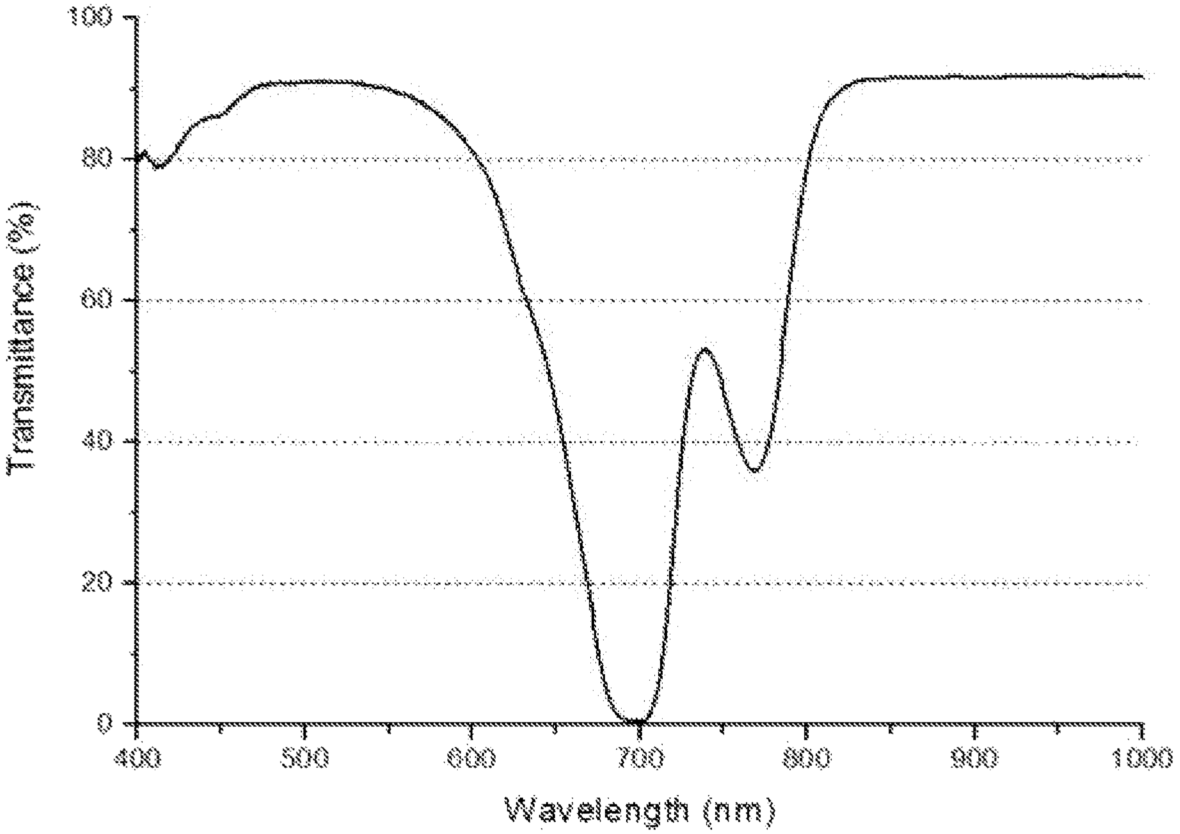

An optical absorption film was formed in the same manner as in Embodiment 10 using the optical absorbent composition. FIG. 6 is a spectrum showing the evaluation result of the transmittance of the optical absorption film.

Embodiments 10 and 11 and Comparative Example 6 were evaluated for absorption characteristics in a wavelength range of 600 nm to 900 nm, and the results are summarized in Table 3.

In Table 3, T50% cut-on is the shortest wavelength showing about 50% transmittance within the wavelength range of 600 nm to 900 nm in the transmittance spectrum. T50% cut-off is the longest wavelength showing about 50% transmittance within the wavelength range of 600 nm to 900 nm in the transmittance spectrum.

In Table 3, T20% cut-on is the shortest wavelength showing about 20% transmittance within the wavelength range of 600 nm to 900 nm in the transmittance spectrum. T20% cut-off is the longest wavelength showing about 20% transmittance within the wavelength region of 600 nm to 900 nm in the transmittance spectrum.

In Table 3, $T_{MIN}$ is the minimum transmittance observed within the wavelength range of 600 nm to 900 nm. $T_{AVG}$ is the average transmittance within the wavelength range of 600 nm to 900 nm.

TABLE 3

| | Embodiment 10 | Embodiment 11 | Comparative Example 6 |
|---|---|---|---|
| T50% cut-on (nm) | 635.8 | 635.8 | 647.0 |
| T50% cut-off (nm) | 804.9 | 798.4 | 783.0 |
| T20% cut-on (nm) | 667.8 | 662.9 | 669.4 |
| T20% cut-off (nm) | 789.2 | 788.3 | 717.7 |
| 600 nm~900 nm $T_{MIN}$ (%) | 0.58 | 0.18 | 0.59 |
| $T_{AVG}$ (%) | 42.6 | 44.3 | 57.6 |

The invention claimed is:

1. An optical absorbent composition comprising:

a first chemical compound represented by Chemical Formula 1:

[Chemical Formula 1]

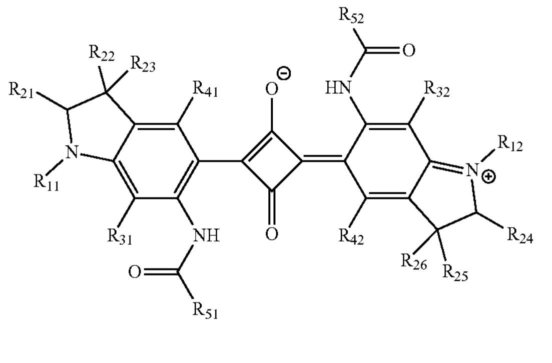

wherein $R_{11}$, $R_{12}$, $R_{51}$ and $R_{52}$ are each independently an alkyl group, a haloalkyl group, an alkoxy group, or an alkoxyalkyl group and $R_{21}$, $R_{22}$, $R_{23}$, $R_{24}$, $R_{25}$, $R_{26}$, $R_{31}$, $R_{32}$, $R_{41}$ and $R_{42}$ are each independently hydrogen, an alkyl group, an alkoxy group, or an alkoxyalkyl group in Chemical Formula 1, wherein the first chemical compound satisfies any one of Condition 1 and Condition 2:

Condition 1: a sum of carbon numbers of $R_{11}$, $R_{12}$, $R_{51}$, $R_{52}$, $R_{21}$, $R_{22}$, $R_{23}$, $R_{24}$, $R_{25}$, $R_{26}$, $R_{31}$, $R_{32}$, $R_{41}$ and $R_{42}$ in Chemical Formula 1 is 16 or more; and Condition 2: a sum of carbon numbers of $R_{11}$, $R_{12}$, $R_{51}$, $R_{52}$, $R_{21}$, $R_{22}$, $R_{23}$, $R_{24}$, $R_{25}$, $R_{26}$, $R_{31}$, $R_{32}$, $R_{41}$ and $R_{42}$ in Chemical Formula 1 is 14 or more, and at least one of $R_{11}$, $R_{12}$, $R_{51}$, $R_{52}$, $R_{21}$, $R_{22}$, $R_{23}$, $R_{24}$, $R_{25}$, $R_{26}$, $R_{31}$, $R_{32}$, $R_{41}$ and $R_{42}$ is an alkoxy group or an alkoxyalkyl group; and a second chemical compound represented by Chemical Formula 2:

[Chemical Formula 2]

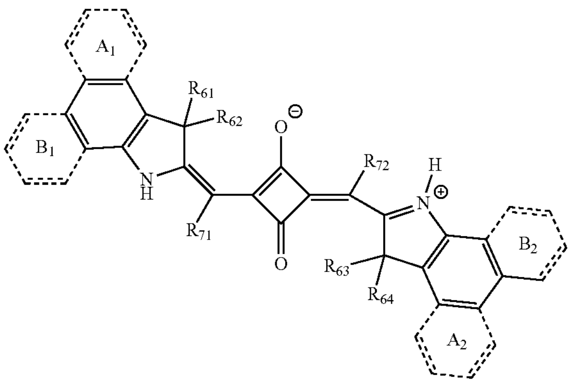

wherein $R_{71}$ and $R_{72}$ are each independently an alkyl group, an alkoxy group, or an alkoxyalkyl group, $R_{61}$ to $R_{64}$ are each independently hydrogen, an alkyl group, an alkoxy group, or an alkoxyalkyl group, and $A_1$, $B_1$, $A_2$ and $B_2$ are each independently a benzene structure or absent in Chemical Formula 2, wherein the second chemical compound satisfies any one of Condition 3 and Condition 4:

Condition 3: a sum of carbon numbers of $R_{61}$, $R_{62}$, $R_{63}$, $R_{64}$, $R_{71}$ and $R_{72}$ in Chemical Formula 2 is 10 or more; and Condition 4: a sum of carbon numbers of $R_{61}$, $R_{62}$, $R_{63}$, $R_{64}$, $R_{71}$ and $R_{72}$ is 4 or more, and at least one of $R_{61}$, $R_{62}$, $R_{63}$, $R_{64}$, $R_{71}$, and $R_{72}$ is an alkoxy group or an alkoxyalkyl group in Chemical Formula 2.

2. The optical absorbent composition of claim 1, wherein $R_{21}$, $R_{22}$, $R_{23}$, $R_{24}$, $R_{25}$ and $R_{26}$ in Chemical Formula 1 are each independently an alkyl group, an alkoxy group, or an alkoxyalkyl group and $R_{31}$, $R_{32}$, $R_{41}$ and $R_{42}$ is hydrogen.

3. The optical absorbent composition of claim 1, wherein a ratio (C1/C5) of a sum of carbon numbers of $R_{11}$ and $R_{12}$ (C1) to a sum of carbon numbers of $R_{51}$ and $R_{52}$ (C5) in Chemical Formula 1 is in a range of 0.1 to 10.

4. The optical absorbent composition of claim 1, wherein a ratio (C1/C2) of a sum of carbon numbers of $R_{11}$ and $R_{12}$ (C1) to a sum of carbon numbers of $R_{21}$ to $R_{26}$, $R_{31}$, $R_{32}$, $R_{41}$ and $R_{42}$ (C2) in Chemical Formula 1 is in a range of 1 to 10.

5. The optical absorbent composition of claim 1, wherein a ratio (C7/C6) of a sum of carbon numbers of $R_{71}$ and $R_{72}$ (C7) to a sum of carbon numbers of $R_{61}$ to $R_{64}$ (C6) in Chemical Formula 2 is in a range of 0.1 to 10.

6. The optical absorbent composition of claim 1, wherein one of $A_1$ and $B_1$ is a benzene structure and the other is absent, and one of $A_2$ and $B_2$ is a benzene structure and the other is absent in Chemical Formula 2.

7. The optical absorbent composition of claim 1, wherein a ratio (C1/C7) of a sum of carbon numbers of $R_{11}$ and $R_{12}$ (C1) in Chemical Formula 1 to a sum of carbon numbers of $R_{71}$ and $R_{72}$ (C7) in Chemical Formula 2 is in a range of 0.1 to 10.

8. The optical absorbent composition of claim 1, wherein a ratio (CA/CB) of a sum of carbon numbers of $R_{11}$, $R_{12}$, $R_{51}$, $R_{52}$, $R_{21}$, $R_{22}$, $R_{23}$, $R_{24}$, $R_{25}$, $R_{26}$, $R_{31}$, $R_{32}$, $R_{41}$ and $R_{42}$ (CA) to a sum of carbon numbers of $R_{61}$, $R_{62}$, $R_{63}$, $R_{64}$, $R_{71}$ and $R_{72}$ (CB) is in a range of 0.5 to 5.

9. The optical absorbent composition of claim 1, wherein the optical absorbent composition comprises 1 to 500 parts by weight of the second chemical compound with respect to 100 parts by weight of the first chemical compound.

10. The optical absorbent composition of claim 1 further comprising a resin component.

11. The optical absorbent composition of claim 1 further comprising a solvent.

12. An optical absorption film comprising:

a resin;

a third chemical compound represented by Chemical Formula 1:

[Chemical Formula 1]

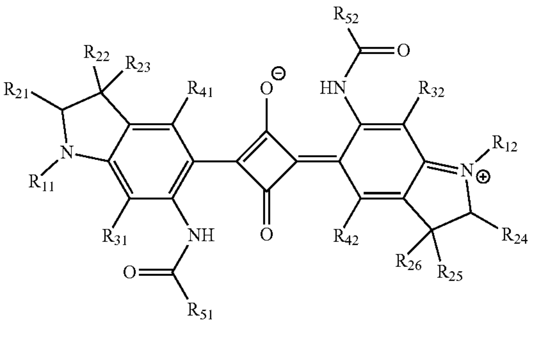

wherein $R_{11}$, $R_{12}$, $R_{51}$ and $R_{52}$ are each independently an alkyl group, haloalkyl group, alkoxy group or alkoxyalkyl group, and $R_{21}$, $R_{22}$, $R_{23}$, $R_{24}$, $R_{25}$, $R_{26}$, $R_{31}$, $R_{32}$, $R_{41}$ and $R_{42}$ are each independently hydrogen, an alkyl group, an alkoxy group, or an alkoxyalkyl group in Chemical Formula 1; and a fourth chemical compound represented by Chemical Formula 2:

[Chemical Formula 2]

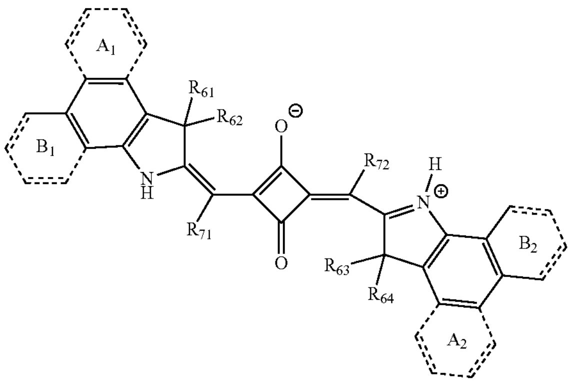

wherein $R_{71}$ and $R_{72}$ are each independently an alkyl group, an alkoxy group, or an alkoxyalkyl group, $R_{61}$ to $R_{64}$ are each independently hydrogen, an alkyl group, an alkoxy group, or an alkoxyalkyl group, and $A_1$, $B_1$, $A_2$ and $B_2$ are each independently a benzene structure or absent in Chemical Formula 2.

13. The optical absorption film of claim 12, wherein an absorption band exhibits a bandwidth of 60 nm or more in a wavelength range of 600 nm to 900 nm.

14. The optical absorption film of claim 12, wherein the resin component comprises one or more selected from a group consisted of a cyclo olefin polymer (COP)-based resin, polyarylate resin, polysulfone resin, polyether sulfone resin, polyparaphenylene resin, polyarylene ether phosphine oxide resin, polyimide resin, polyetherimide resin, polyamideimide resin, acrylic resin, polycarbonate resin, polyethylene naphthalate resin, and silicone resin.

15. The optical absorption film of claim 12, wherein a T50% cut-on wavelength is in a wavelength range of 600 nm to 800 nm.

16. The optical absorption film of claim 12, wherein a T50% cut-off wavelength is in a wavelength range of 700 nm to 900 nm.

17. The optical absorption film of claim 12, wherein the optical absorption film comprises 0.5 to 50 parts by weight of the third chemical compound with respect to 100 parts by weight of the resin component.

18. The optical absorption film of claim 12, wherein the optical absorption film comprises 0.5 to 50 parts by weight of the fourth chemical compound with respect to 100 parts by weight of the resin component.

19. An optical filter comprising:

a substrate; and an optical absorption film formed on one or both surfaces of the substrate wherein the optical absorption film further comprises a resin; a fifth chemical compound represented by Chemical Formula 1:

[Chemical Formula 1]

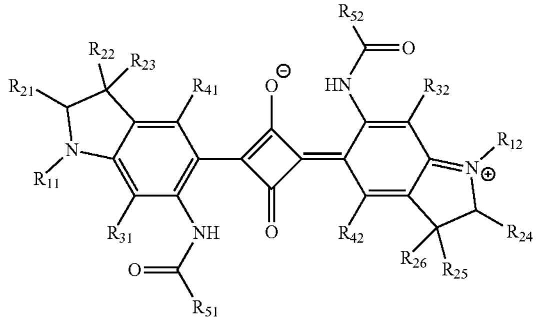

wherein $R_{11}$, $R_{12}$, $R_{51}$ and $R_{52}$ are each independently an alkyl group, a haloalkyl group, an alkoxy group, or an alkoxyalkyl group and $R_{21}$, $R_{22}$, $R_{23}$, $R_{24}$, $R_{25}$, $R_{26}$, $R_{31}$, $R_{32}$, $R_{41}$ and $R_{42}$ are each independently hydrogen, an alkyl group, an alkoxy group, or an alkoxyalkyl group in Chemical Formula 1; and a sixth chemical compound represented by Chemical Formula 2:

[Chemical Formula 2]

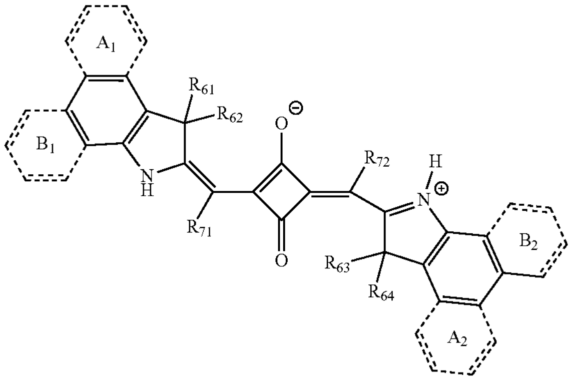

wherein $R_{71}$ and $R_{72}$ are each independently an alkyl group, an alkoxy group, or an alkoxyalkyl group, $R_{61}$ to $R_{64}$ are each independently hydrogen, an alkyl group, an alkoxy group, or an alkoxyalkyl group, and $A_1$, $B_1$, $A_2$ and $B_2$ are each independently a benzene structure or absent in Chemical Formula 2.

20. The optical filter of claim 19, further comprising a dielectric film wherein a shortest wavelength exhibiting a reflectance of 50% in a wavelength range of 600 nm to 900 nm in the dielectric film is about 710 nm or more or absent.

* * * * *